(12) United States Patent
Kubo et al.

(10) Patent No.: US 11,103,287 B1
(45) Date of Patent: Aug. 31, 2021

(54) PEDICLE SCREW AND MULTI-AXIAL CONNECTOR SYSTEM

(71) Applicant: Choice Spine, LLC, Knoxville, TN (US)

(72) Inventors: Matthew B. Kubo, Knoxville, TN (US); Michael James Brow, Knoxville, TN (US); Benjamin G. Harder, Knoxville, TN (US); Corey Allen Johnson, Rochester, MN (US)

(73) Assignee: Choice Spine, LLC, Knoxville, TN (US)

( * ) Notice: Subject to any disclaimer, the term of this patent is extended or adjusted under 35 U.S.C. 154(b) by 24 days.

(21) Appl. No.: 16/263,027

(22) Filed: Jan. 31, 2019

Related U.S. Application Data

(62) Division of application No. 15/078,327, filed on Mar. 23, 2016, now Pat. No. 10,219,840.

(60) Provisional application No. 62/143,480, filed on Apr. 6, 2015.

(51) Int. Cl.
*A61B 17/70* (2006.01)

(52) U.S. Cl.
CPC ...... *A61B 17/7041* (2013.01); *A61B 17/7037* (2013.01)

(58) Field of Classification Search
CPC .......................................... A61B 17/70–7052
See application file for complete search history.

(56) References Cited

U.S. PATENT DOCUMENTS

| | | | |
|---|---|---|---|
| 7,575,587 B2 | 8/2009 | Rezach et al. | |
| 8,147,523 B2 | 4/2012 | Miller et al. | |
| 8,246,657 B1* | 8/2012 | Samuel | A61B 17/7049 606/250 |
| 8,480,713 B2 | 7/2013 | Rezach | |
| 8,585,741 B2 | 11/2013 | Gabelberger et al. | |
| 10,219,840 B2* | 3/2019 | Kubo | A61B 17/7041 |
| 2003/0100904 A1 | 5/2003 | Biedermann | |
| 2006/0058787 A1* | 3/2006 | David | A61B 17/7041 606/256 |
| 2006/0149235 A1 | 7/2006 | Jackson | |
| 2007/0118118 A1 | 5/2007 | Kwak et al. | |

(Continued)

OTHER PUBLICATIONS

International Searching Authority, International Search Report, dated Aug. 29, 2016, PCT/US16/25811.

*Primary Examiner* — Nicholas J Plionis
(74) *Attorney, Agent, or Firm* — Luedeka Neely Group, PC

(57) ABSTRACT

A posterior spinal implant system configured to immobilize and stabilize spinal segments as an adjunct to fusion in the thoracic, lumbar, and/or sacral spine. The implant system includes a pedicle screw, a spinal rod; a connector connecting the pedicle screw to the spinal rod. The connector includes a connector body, a polyaxial screw receiver positioned on the connector body and configured to receive the pedicle screw and permit polyaxial orientation of the connector relative to the pedicle screw, a polyaxial rod receiver positioned in the connector body and configured to receive the spinal rod and permit polyaxial orientation of the spinal rod relative to the connector, and a lock installed in the polyaxial rod receiver. The lock is operable to lock the connector relative the pedicle screw, lock the polyaxial rod receiver relative to the connector, and lock the spinal rod relative to the polyaxial rod receiver.

11 Claims, 34 Drawing Sheets

(56) References Cited

U.S. PATENT DOCUMENTS

2009/0204155 A1* 8/2009 Aschmann ......... A61B 17/7032
                                                    606/264
2011/0106174 A1   5/2011 Rezach
2011/0218579 A1   9/2011 Jackson
2014/0088650 A1   3/2014 Taddia et al.

* cited by examiner

PEDICLE SCREW AND MULTI-AXIAL CONNECTOR SYSTEM

CROSS-REFERENCE TO RELATED APPLICATION

This application claims priority to U.S. Provisional Application Ser. No. 62/143,480 filed Apr. 6, 2015, and entitled "Pedicle Screw And Multi-Axial Connector System," incorporated by reference herein in its entirety.

FIELD

The present disclosure relates to posterior spinal implant systems. More particularly, the disclosure relates to implant systems having a pedicle screw, a spinal rod, and multi-axial connector between the rod and the screw. The implant systems are positionable to immobilize and stabilize spinal segments as an adjunct to fusion in the thoracic, lumbar, and/or sacral spine.

BACKGROUND

Improvement is desired in the construction and efficiency of posterior spinal implants for immobilizing and stabilizing spine segments. Current devices desire improvement in that it is difficult to make adjustments to the orientation of the components, and then to lock the relative orientations.

In particular, what is desired is a spinal implant that enables adjustment of the relative orientations of the components, and to quickly and easily lock the relative positions of the components.

SUMMARY

The disclosure advantageously provides posterior spinal implant systems configured to immobilize and stabilize spinal segments as an adjunct to fusion in the thoracic, lumbar, and/or sacral spine. The systems are advantageously operable to permit adjustment of the relative orientations of a spinal rod and a pedicle screw, and to quickly and easily lock the relative positions of the spinal rod and the pedicle screw.

In one aspect, an implant system according to the disclosure includes a pedicle screw, a spinal rod; a connector connecting the pedicle screw to the spinal rod. The connector includes a connector body, a polyaxial screw receiver positioned in the connector body and configured to receive the pedicle screw and permit polyaxial orientation of the connector relative to the pedicle screw, a polyaxial rod receiver positioned in the connector body and configured to receive the spinal rod and permit polyaxial orientation of the spinal rod relative to the connector, and a lock installed in the polyaxial rod receiver. The lock is operable to lock the connector relative the pedicle screw, lock the polyaxial rod receiver relative to the connector, and lock the spinal rod relative to the polyaxial rod receiver.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
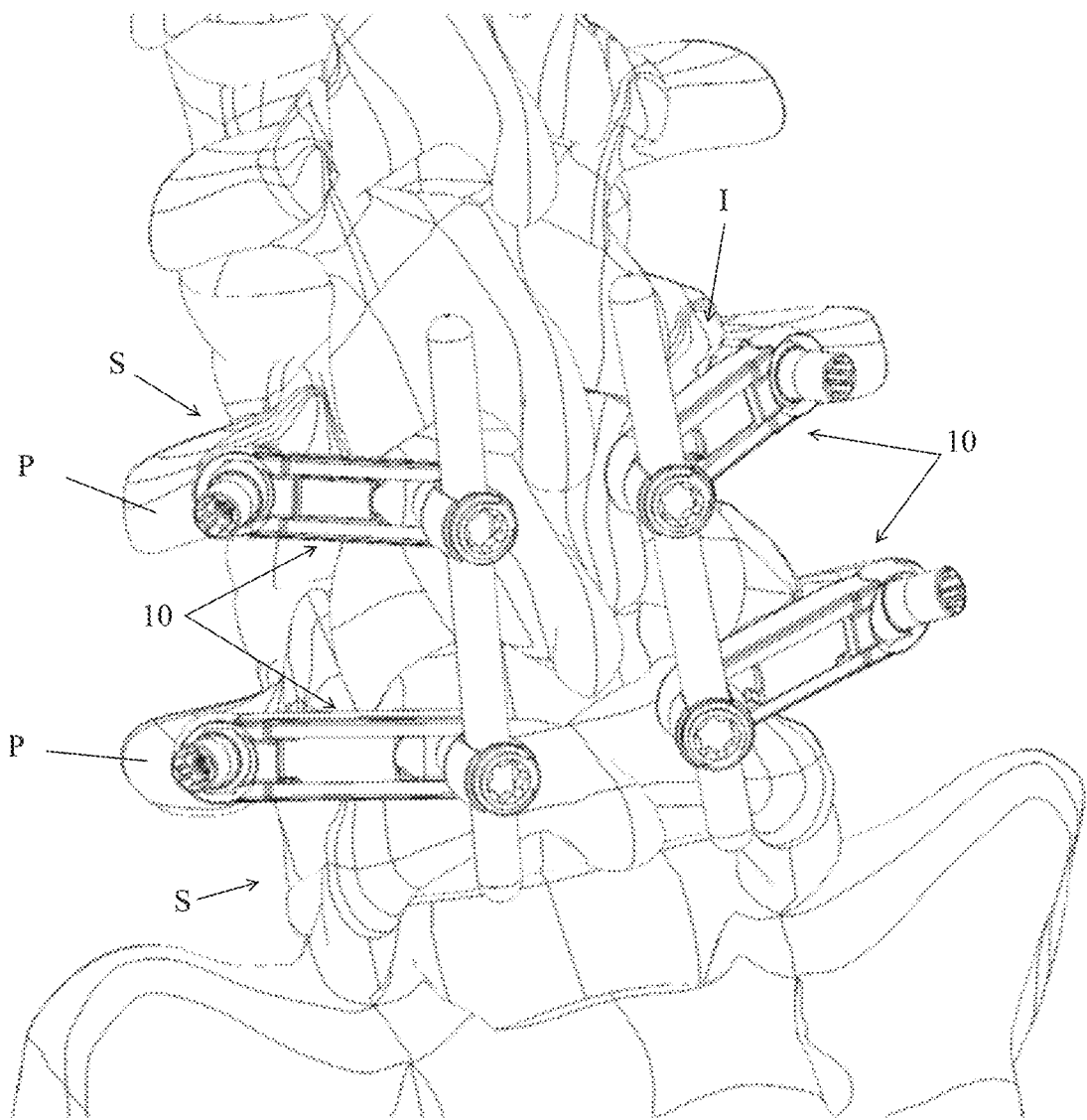
FIGS. 1 and 2 depict a posterior spinal implant system according to the disclosure installed on a spine.
Figure 2:
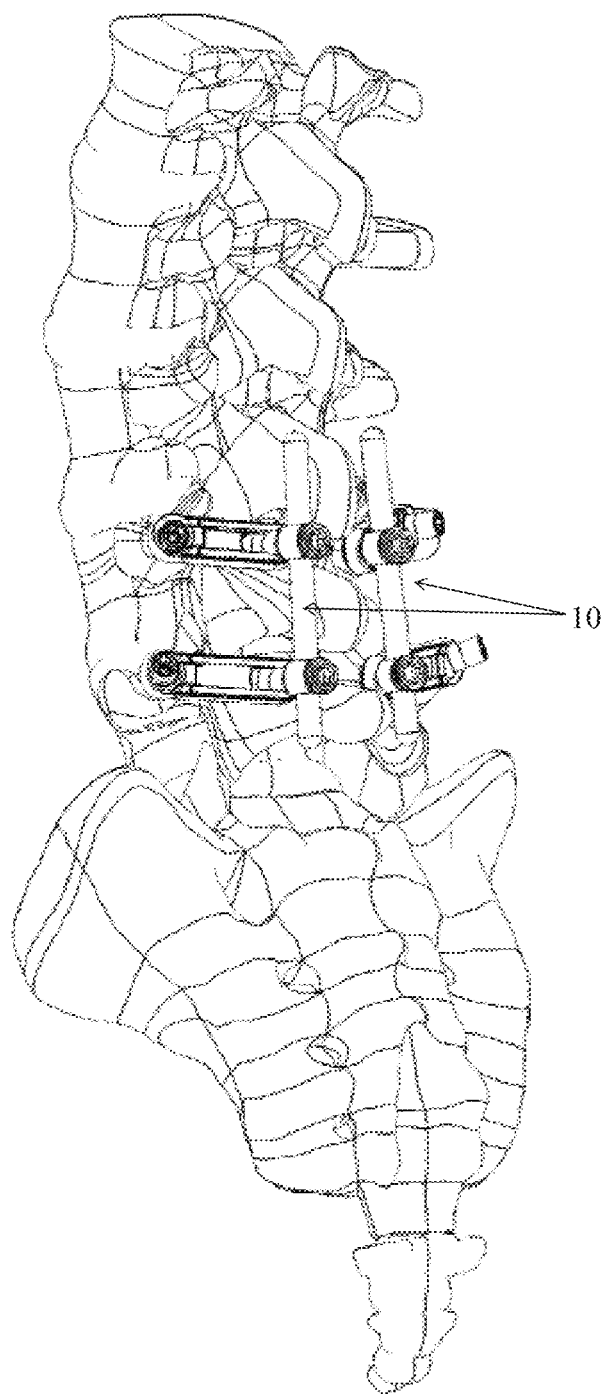
Figure 3:
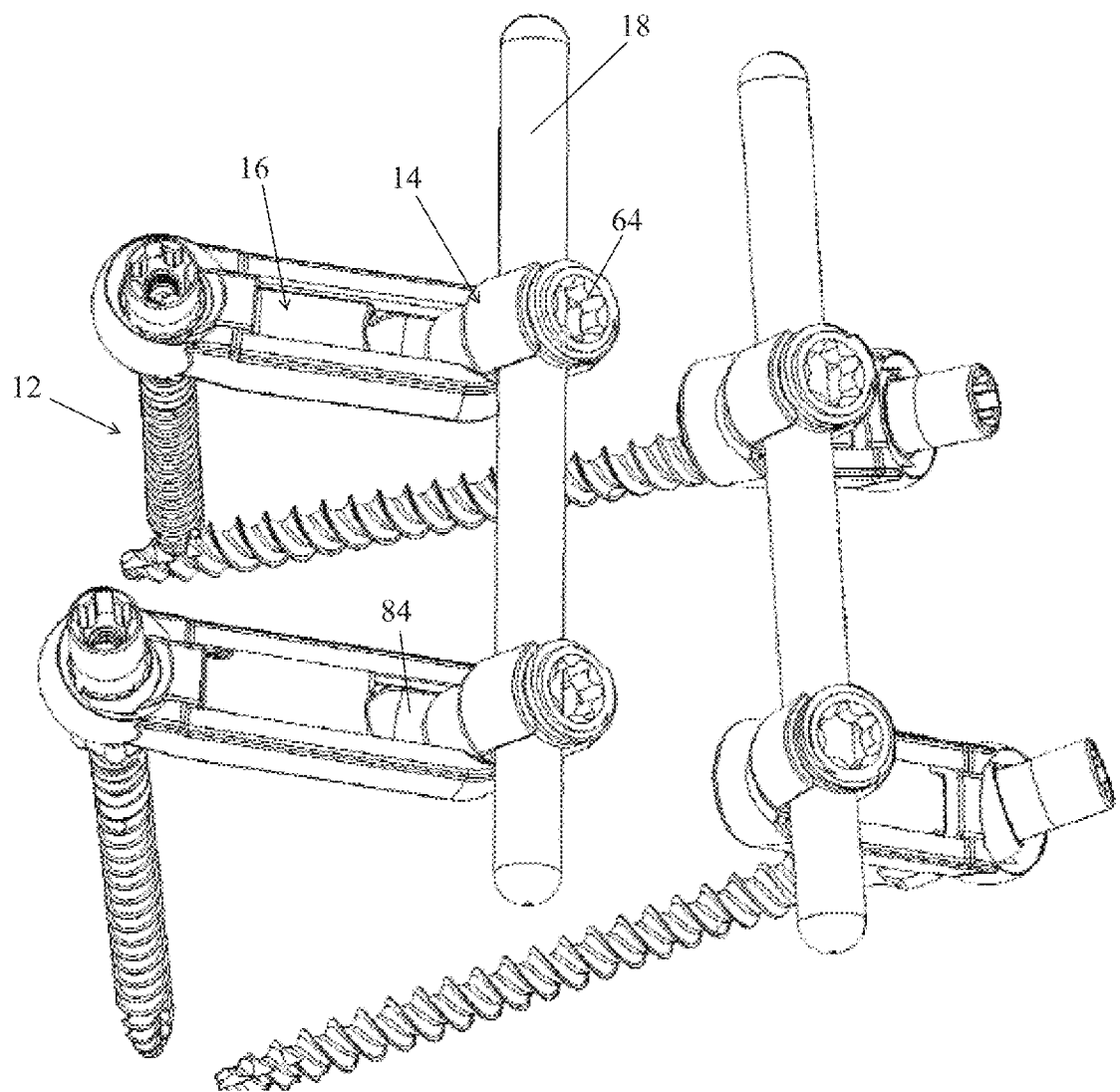
FIGS. 3 and 4 show the system of FIGS. 1 and 2.
Figure 4:
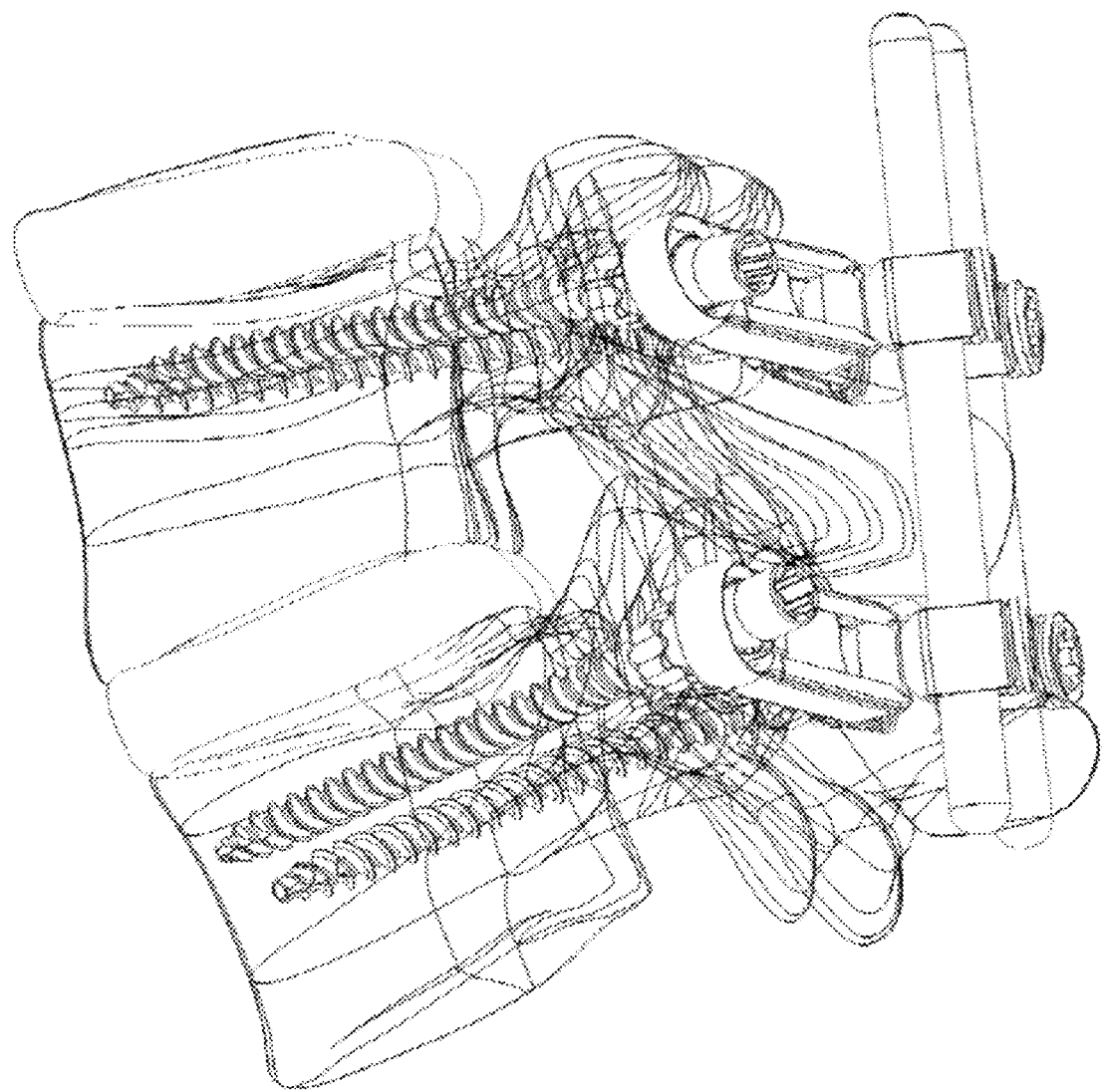
Figure 5:
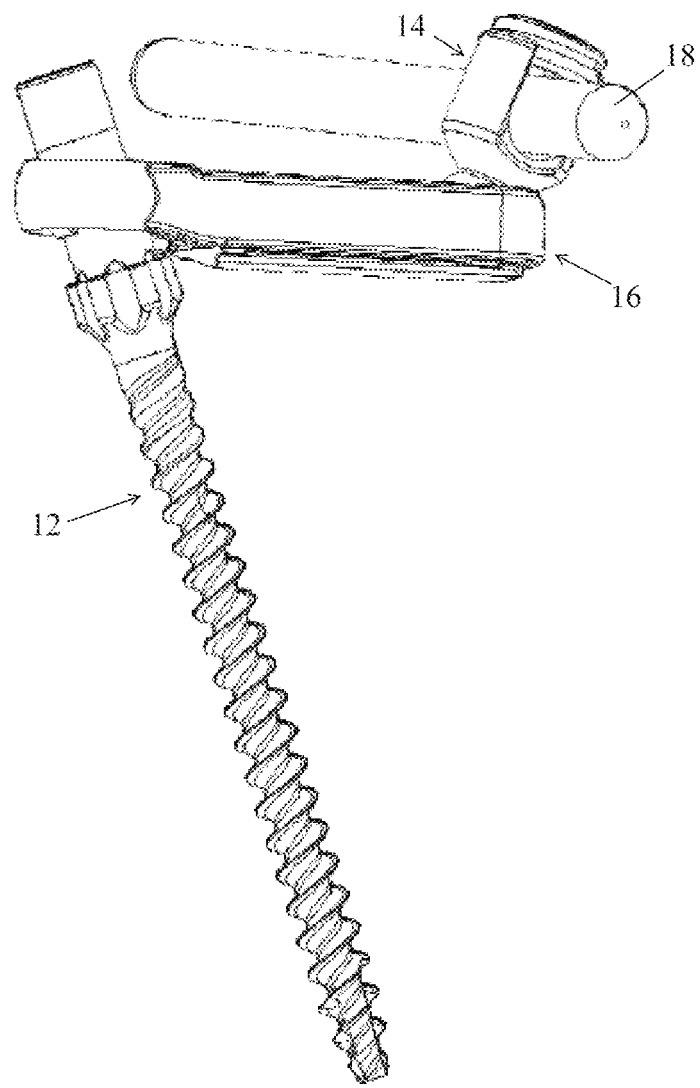
FIG. 5 is an assembled view of components of a posterior spinal implant system of FIGS. 1 and 2.
Figure 6:
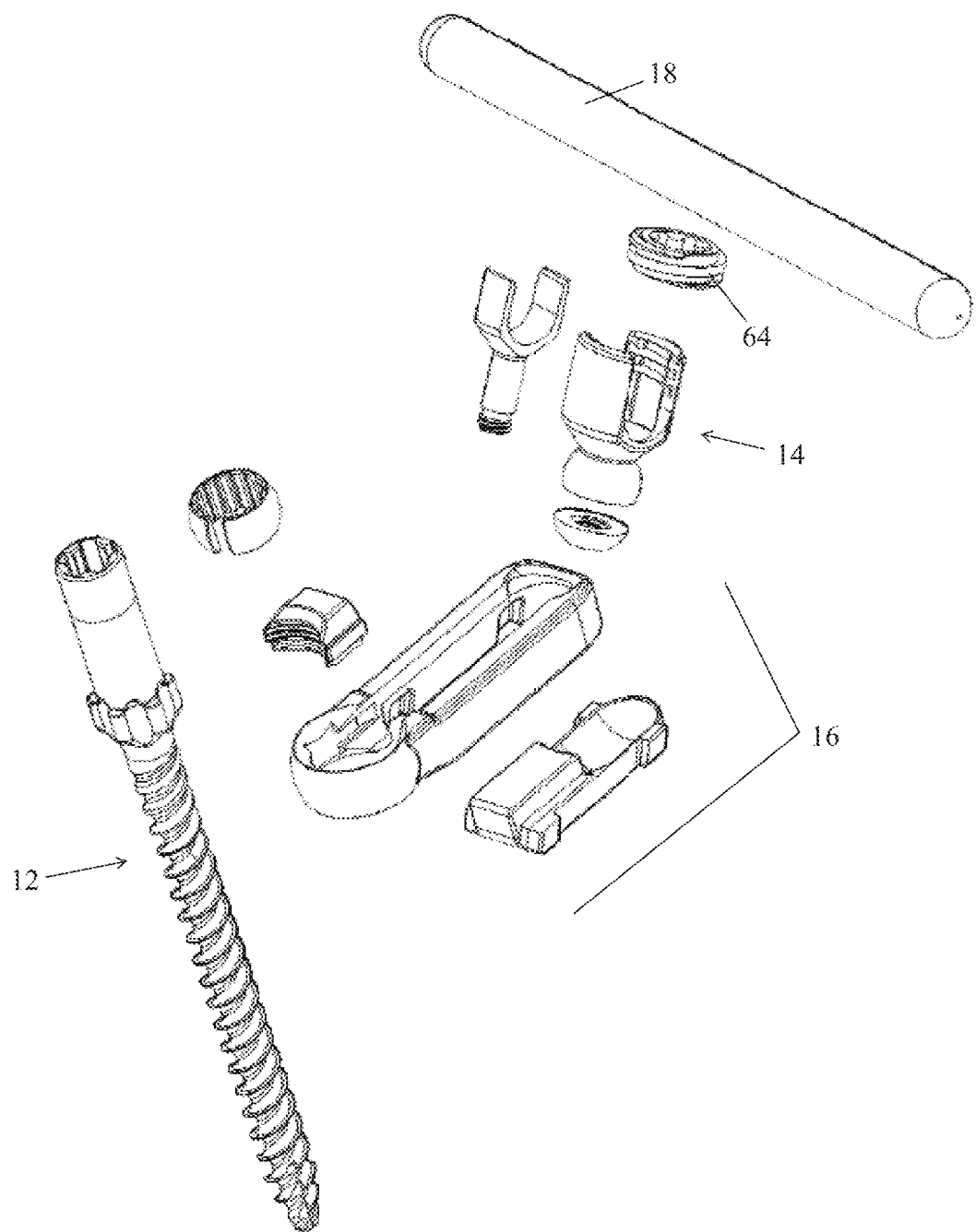
FIGS. 6 and 7 are exploded views of the components of FIG. 5.
Figure 7:
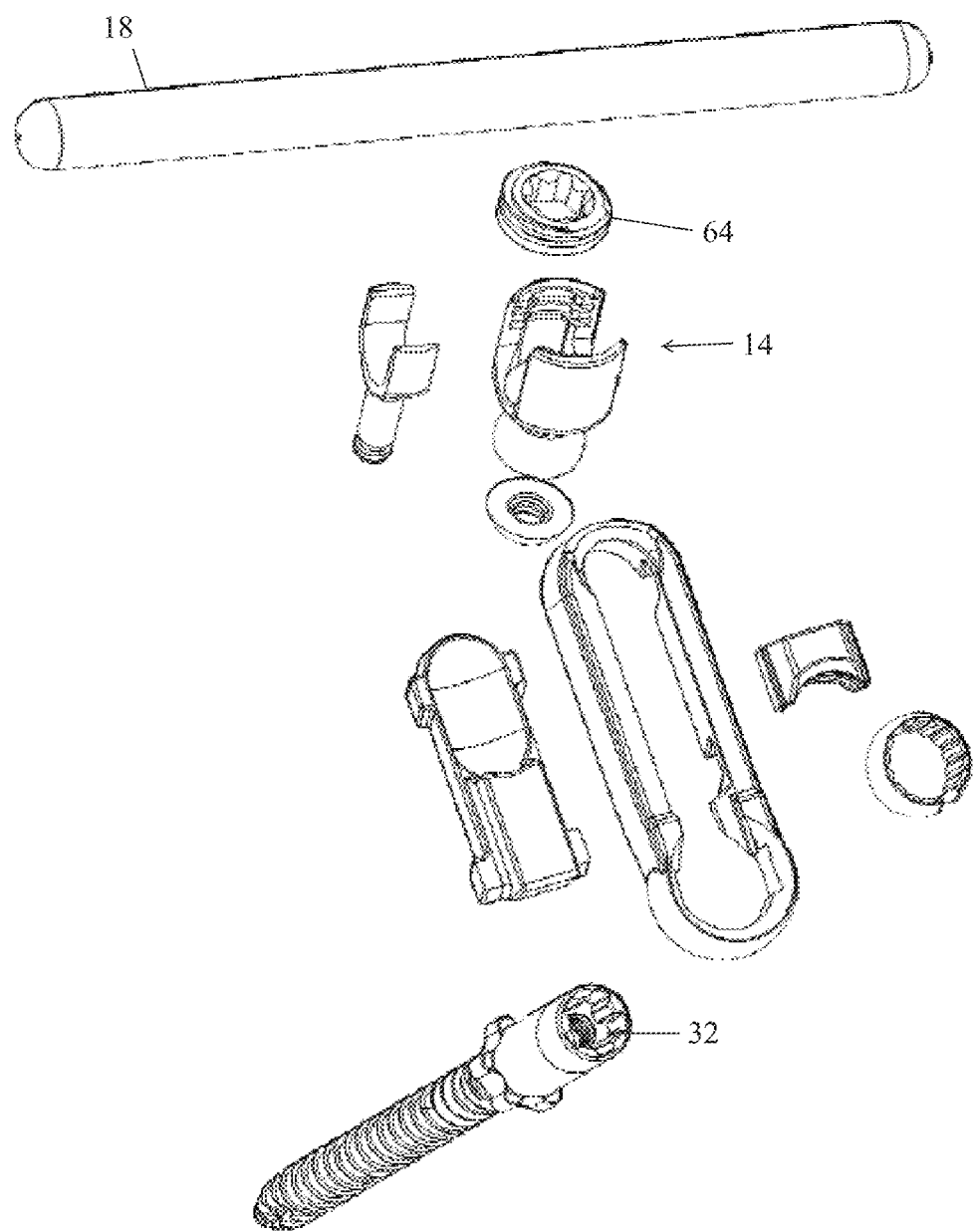
Figure 8:
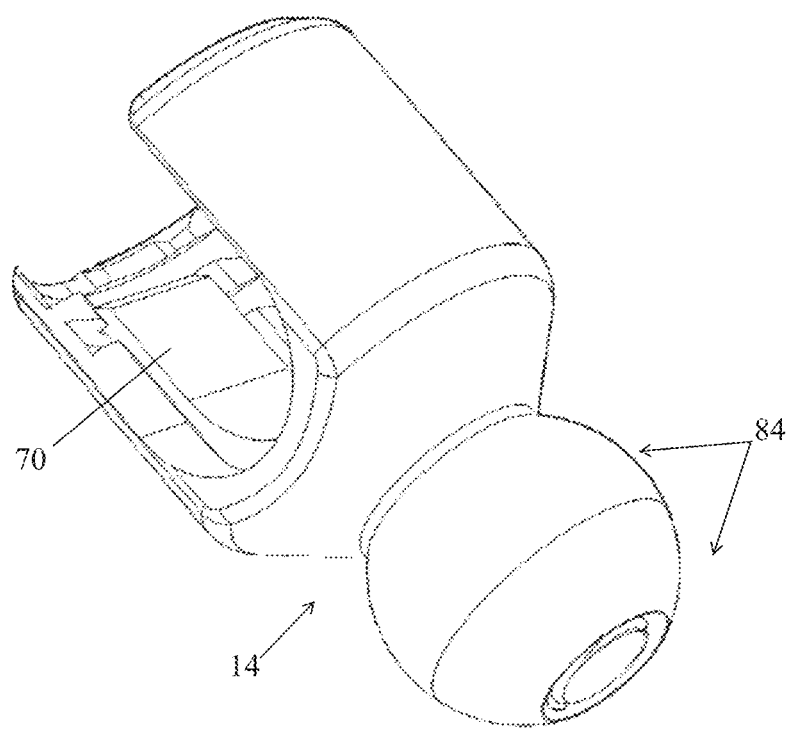
FIGS. 8 and 9 are close up perspective views of a polyaxial rod receiver.
Figure 9:
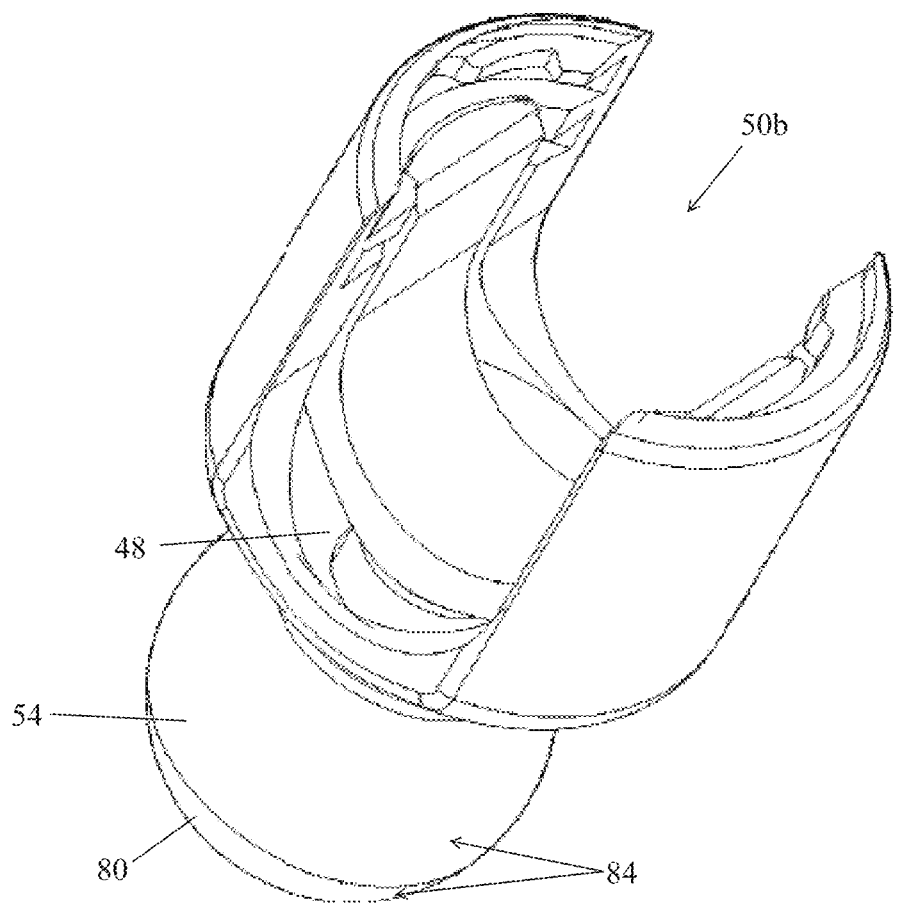
Figure 10:
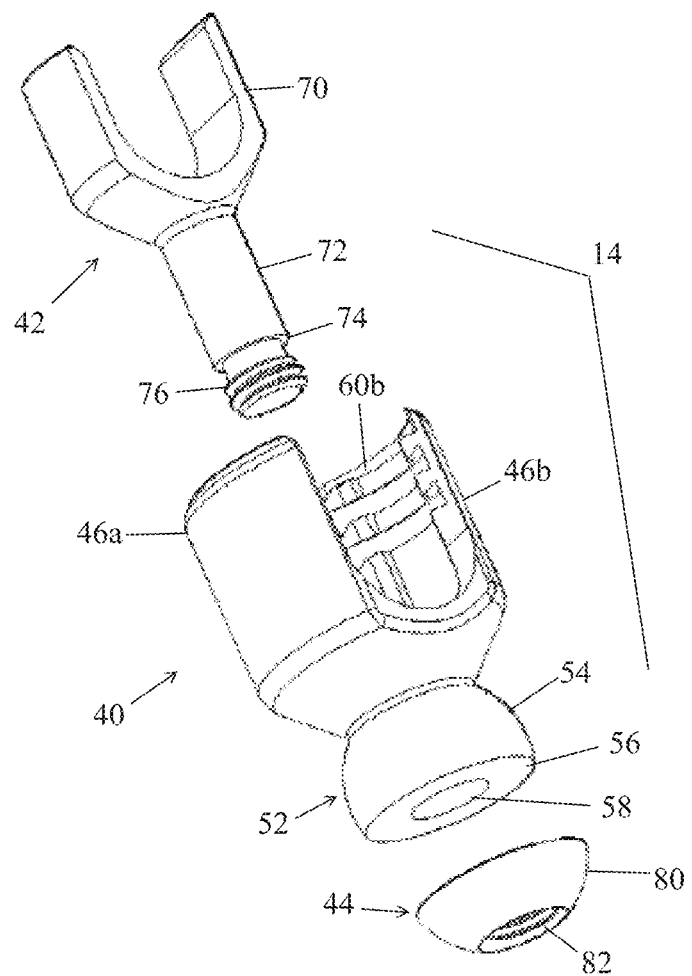
FIG. 10 is an exploded view of the polyaxial rod receiver of FIGS. 8 and 9.
Figure 11:
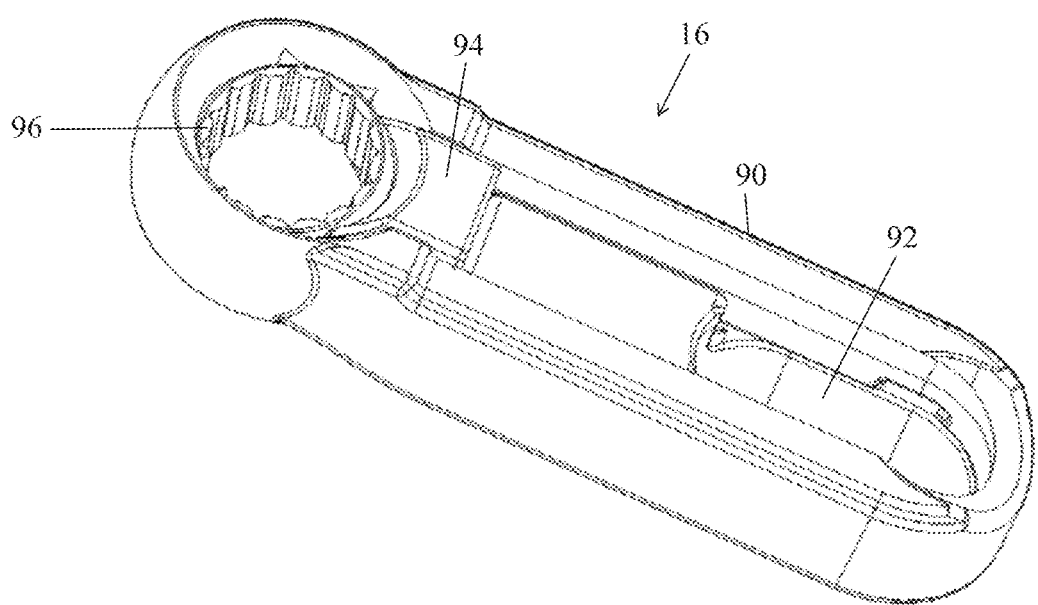
FIG. 11 is a close up perspective view of a connector.
Figure 12:
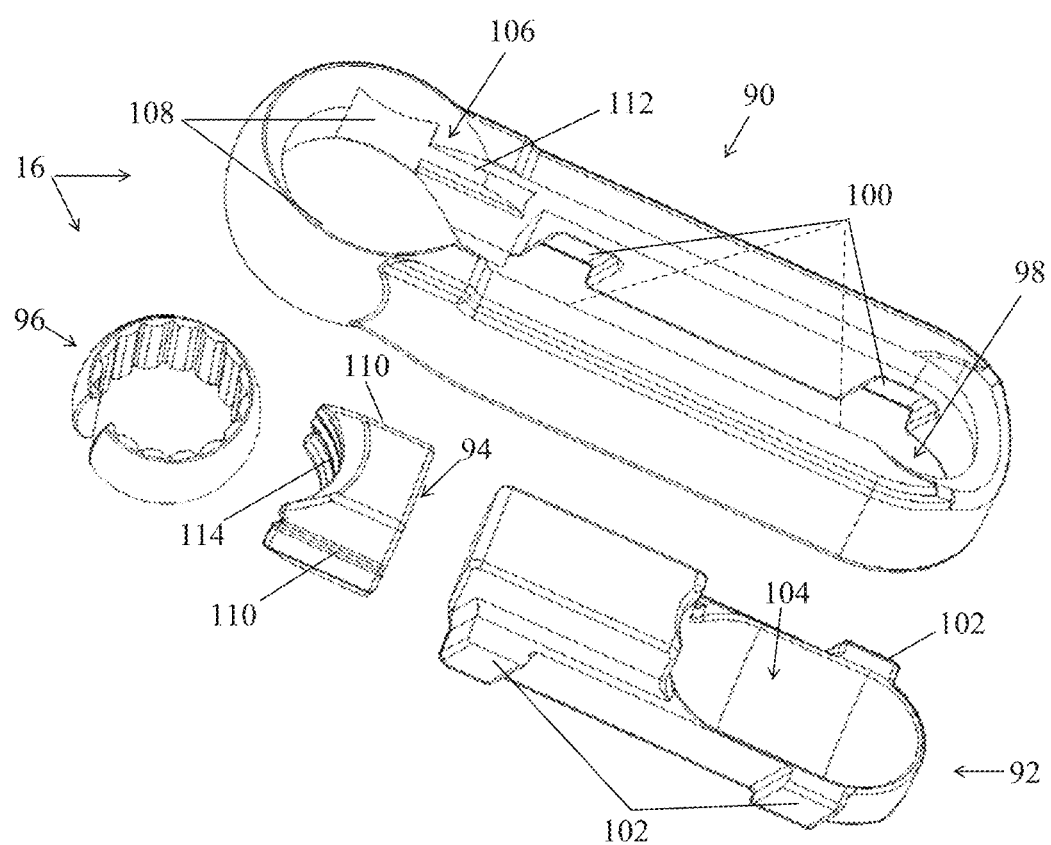
FIG. 12 is an exploded view of the connector of FIG. 11.

With initial reference to FIGS. 1-24, the disclosure relates to a posterior spinal implant system 10. FIGS. 1-2 show a pair implants I each utilizing a pair of the implant systems 10 installed on pedicles P of spinal segments S.

It will be appreciated that a variety of implant configurations may be constructed utilizing the components of the implant systems described herein. The implant systems 10 and the resulting implants I are configured to provide immobilization and stabilization of spinal segments as an adjunct to fusion in the thoracic, lumbar, and/or sacral spine.

The spinal implant system 10 includes, as major components, a pedicle screw 12, a polyaxial rod receiver 14, a connector 16, and a spinal rod 18. Two or more of the implant systems 10 may share a single rod 18 as shown. Each of the components is desirably made of a surgical grade metal.

The pedicle screw 12 is specially configured for use with the implant system 10 and includes a preferably elongated tapered shank 20 having a plurality of threads 22. The pedicle screw 12 also includes an external drive surface 24 and a cannulated post 26 above the external drive surface 24. The cannulated post 26 includes a smooth exterior sidewall 28 and an interior drive surface 30 on the interior sidewall of an interior bore 32.

Figure 24:
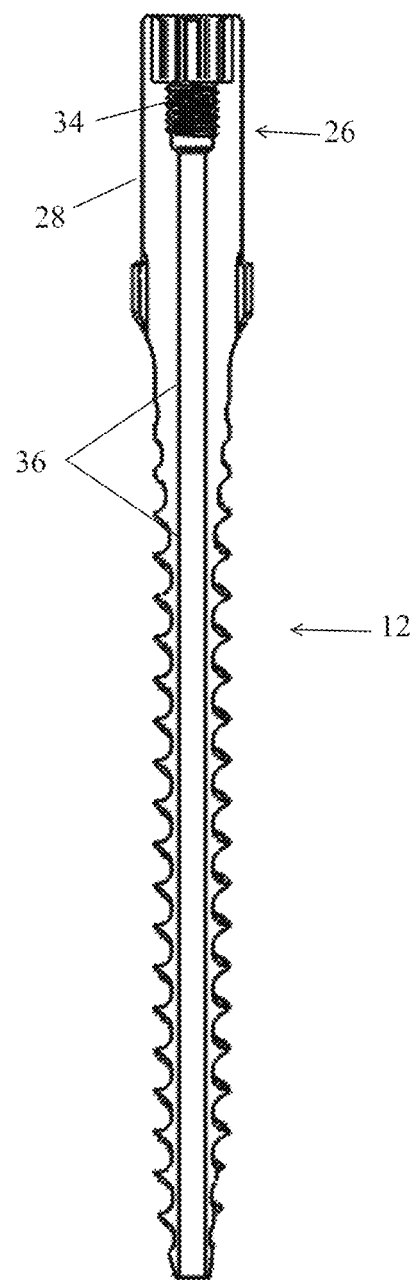
FIG. 24 is a cross-sectional view of a pedicle screw used in the implant system of FIG. 5.

The user will have the option to drive/extract the pedicle screw 12 with the interior drive surface 30 in the post 26, or the external drive surface 24 at the base of the post 26. A threaded receiver 34 (FIGS. 17 and 24) is located at the bottom of the bore 32 of the pedicle screw 12. The threaded receiver 34 provides an attachment point for both internal and external drivers in order to eliminate screw toggle when either of the drivers is attached. The screw 12 may be of solid construction or cannulated to include a central cannula 36 (FIG. 24).

The polyaxial rod receiver 14 is specially configured for use with the implant system 10 and includes a tulip housing 40, a yoke 42, and an end cap 44. The housing 40 includes an interior cavity having sidewalls 46a and 46b and a bottom 48. Aligned U-shaped slots 50a and 50b are formed between the sidewalls 46a and 46b for receiving the rod 18. A central base 52 extends from an exterior lower portion of the housing 40. The base 52 has a curved or spherical exterior sidewall 54 terminating at a flat lower end 56.

A bore 58 extends through the bottom 48 and the base 52 of the polyaxial rod receiver 14 for passage of the yoke 42. Slots 60a and 60b are provided on the interior of the sidewalls 46a and 46b for receiving the yoke 42, and female threads 62a and 62b are located on the interior of the sidewalls 46a and 46b for receiving male threads of a set screw 64 installable on the polyaxial rod receiver 14. The set screw 64 is utilized to lock the spinal rod 18 to the polyaxial rod receiver 14, however, it will be understood that other locking structures may be utilized if desired, to provide a lock structure to lock the spinal rod 18. For example, the polyaxial rod receiver 14 may be configured to utilize other lock structures such as a locking wedge, a cam, caps, luer locks, and other structures configured to mechanically lock the spinal rod 18 in place.

Figure 13:
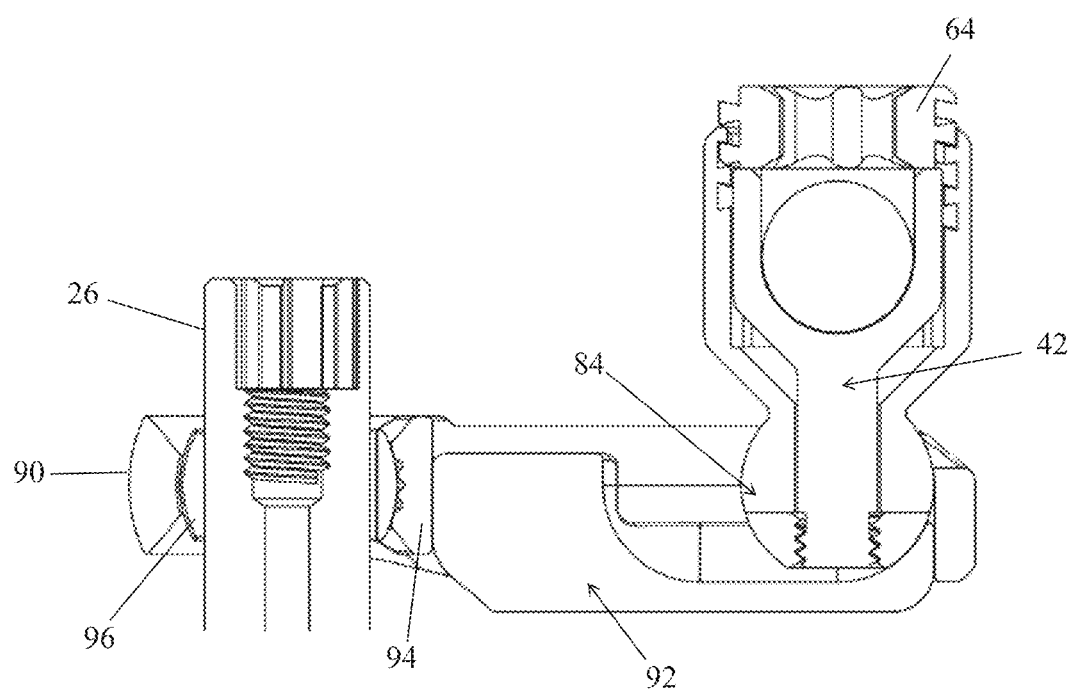
FIG. 13 is a cross-sectional view of the implant system of FIG. 5.
Figure 14:
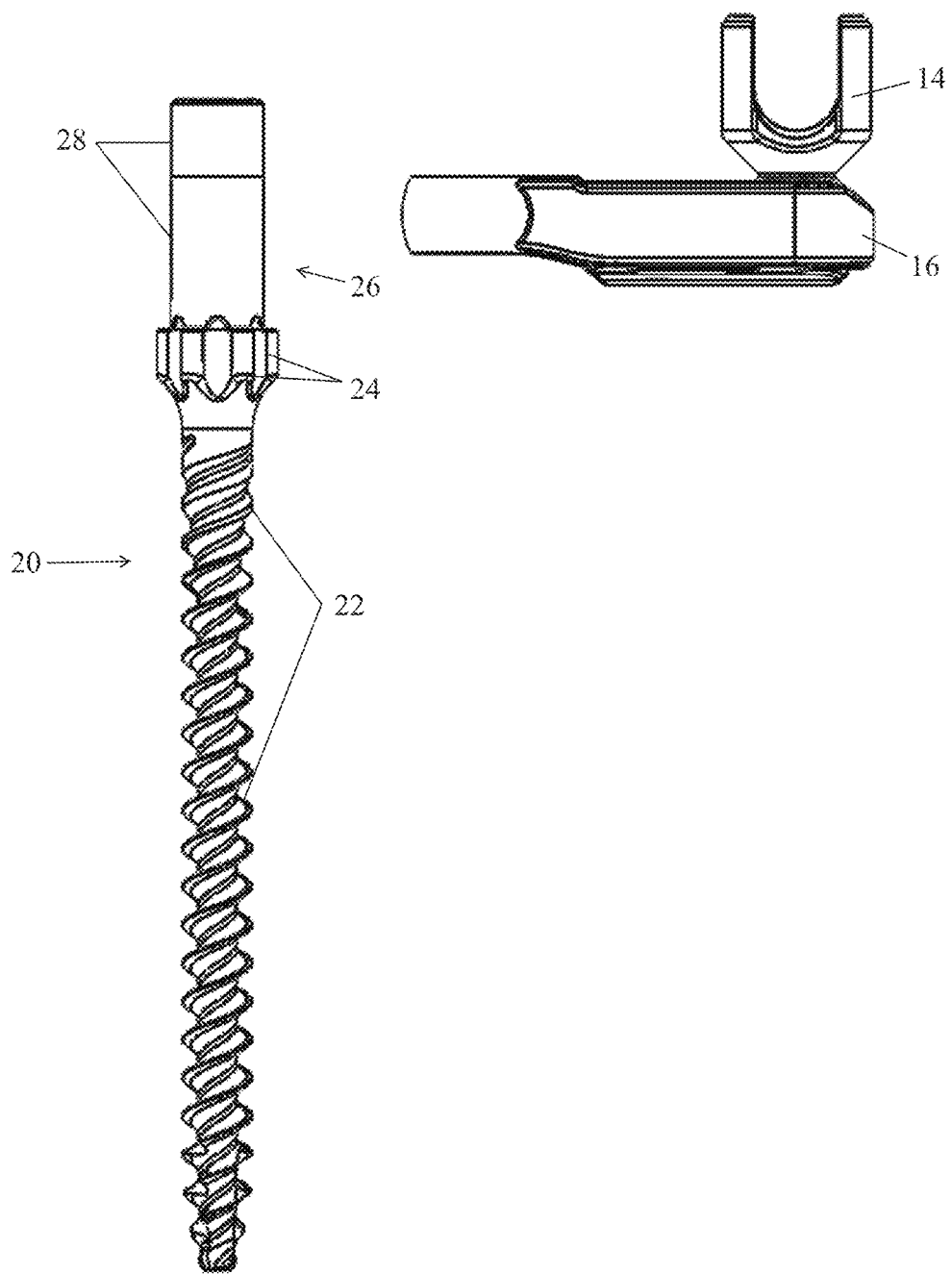
FIG. 14 is a partially exploded of components of the implant system of FIG. 5.
Figure 15:
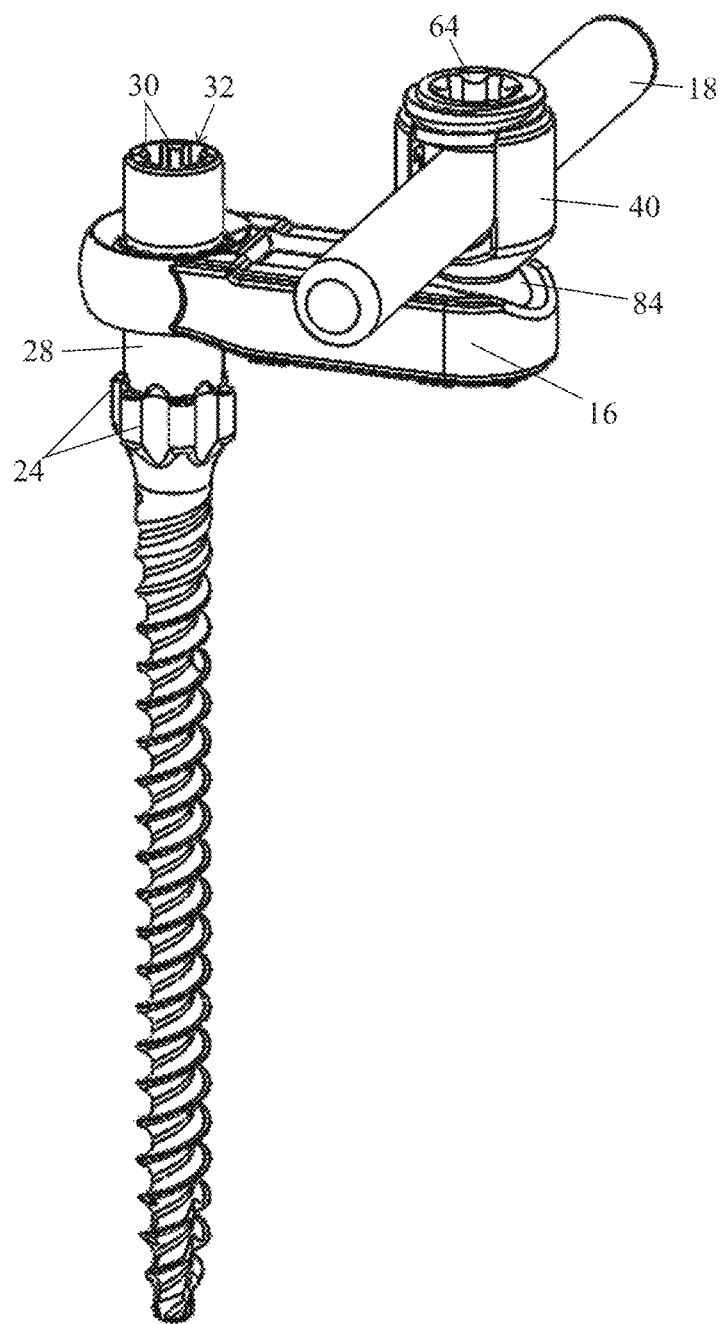
FIG. 15 is another assembled view of the implant system of FIG. 5.

The yoke 42 is a Y-shaped member having an upright 70 and a depending leg 72. The distal end of the leg 72 includes an undercut 74 and threads 76. The end cap 44 includes an external curved or spherical sidewall 80 and internally threaded bore 82. The bore 82 aligns with the bore 58 and threads onto the threads 76 of the leg 72 of the yoke 42, with the cap 44 seating to the undercut 74. When the end cap 44 is installed on the yoke 42, the spherical sidewall 54 of the base 52 of the housing 40 and the spherical sidewall 80 of the end cap 44 combine to provide a sphere 84 for seating in the connector 16 (FIG. 13).

The connector 16 is specially configured for use with the implant system 10 and includes an elongate body 90, a wedge 92 slidingly located in the body 90, a piston 94, and a polyaxial screw receiver 96.

The body 90 of the connector 16 is configured as a generally rectangular ring and includes a rear wedge section 98 for slidingly receiving the wedge 92. The wedge section 98 includes angled slots 100 on the sidewalls thereof for receiving angled projections 102 of the wedge 92. Downward pressure on the wedge 92 will tend to urge the wedge 92 downward and forward corresponding to the travel of the projections 102 in the angled slots 100. The upper inside of the wedge section 98 is cylindrical to match the spherical portion of the polyaxial rod receiver 14.

The upper inside and terminal end of the wedge section 98 is curved/spherical to match the curved/spherical portion of the polyaxial rod receiver 14. The wedge section 92 desirably includes a curved floor 104 for engaging the sphere 84 of the polyaxial rod receiver 14 to facilitate polyaxial range of motion for the sphere 84 of the polyaxial rod receiver 14 relative to the connector 16, including translation or lateral movement of the sphere 84 relative to the connector.

The body 90 includes a forward section 106 forward of the wedge section 98 and configured for receiving the piston 94 and the polyaxial screw receiver 96. The interior sidewalls of the forward section 106 include cut-outs 108 therein to provide a space for inserting the piston 94 and the polyaxial screw receiver 96.

The piston 94 includes a rectangular boss 110 on either side thereof. The bosses 110 align with mating slots 112 on the interior of the body 90 to prevent axial rotation of the piston and provide a track for its lateral movement against the polyaxial screw receiver 96, when the connector 16 is actuated. The piston 94 includes a curved front surface 114 for engaging the polyaxial screw receiver 96. In this regard, the polyaxial screw receiver 96 has a central bore for receiving the pedicle screw 12 and a spherical outer diameter to provide polyaxial screw articulation relative to the connector body 90.

The spinal rod 18 may be provided as by a conventional rod of the type used in conventional posterior spinal implants, and is characterized as a cylindrical solid rod with rounded ends. It will be appreciated that various rod configurations may be utilized.

To install the implant 10 to provide the implant I, the screws 12 are placed in the pedicles P of adjacent ones of the spinal segments S, based on the number of levels or spinal segments to be fused. The connector 16 is placed over the post 26 of each of the screws 12 and is oriented so as to facilitate placement of a spinal rod 18 along the length of the spine, as close to midline of the spine as desired.

The spinal rod 18 is top-loaded, or placed into the tulip housing 40 and the set screw 64 is threaded into the tulip housing 40. The bottom of set screw 64 contacts the rod 18, causing it to press against the yoke 42. The yoke 42 translates inside the tulip housing 40, causing the tulip base 52, to separate from the bottom of the tulip body. A locking force is therefore transmitted through the aforementioned components onto the piston 94. The piston 94 then translates towards the polyaxial screw receiver 96. The load causes the polyaxial screw receiver 96 to collapse around the screw post 26 until locking of all components is achieved. Accordingly, rod and tulip angulation/orientation are locked relative to the body 90 of the connector 16, and the connector/tulip/rod sub-assembly is locked relative to the screw post 26, all in a single step by tightening of the set screw 64.

Orientation of the connectors 16 and the pedicle screws 12 can be adjusted with additional instrumentation to restore proper height and/or orientation of the spinal segments S in order to facilitate proper alignment and fusion of the spine.

Figure 16:
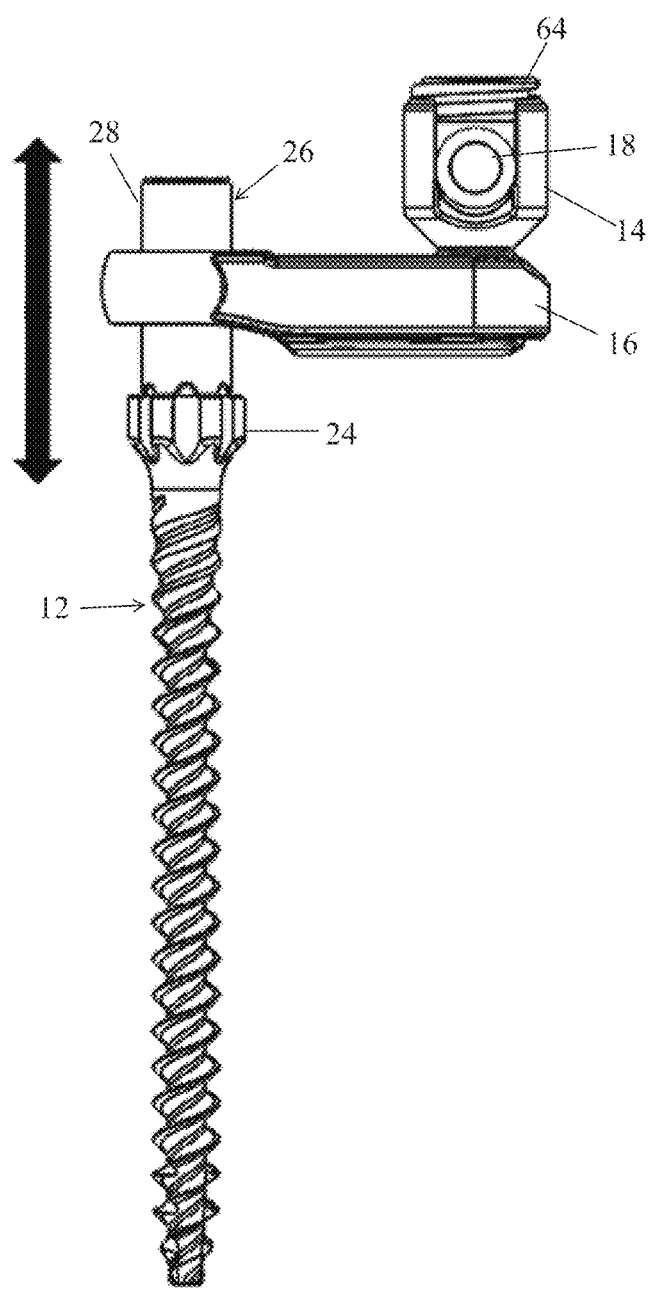
FIG. 16-23 illustrates relative movements of the components of the implant system of FIG. 5.

As depicted in FIGS. 16-23, the connectors 16 can be adjusted to and locked in a plurality of orientations and configurations in order to accommodate each patient's spinal anatomy. For example, as represented in FIG. 16, the system 10 enables vertical adjustment of the connector 16 on the post 26 of the screw 12.

Figure 17:
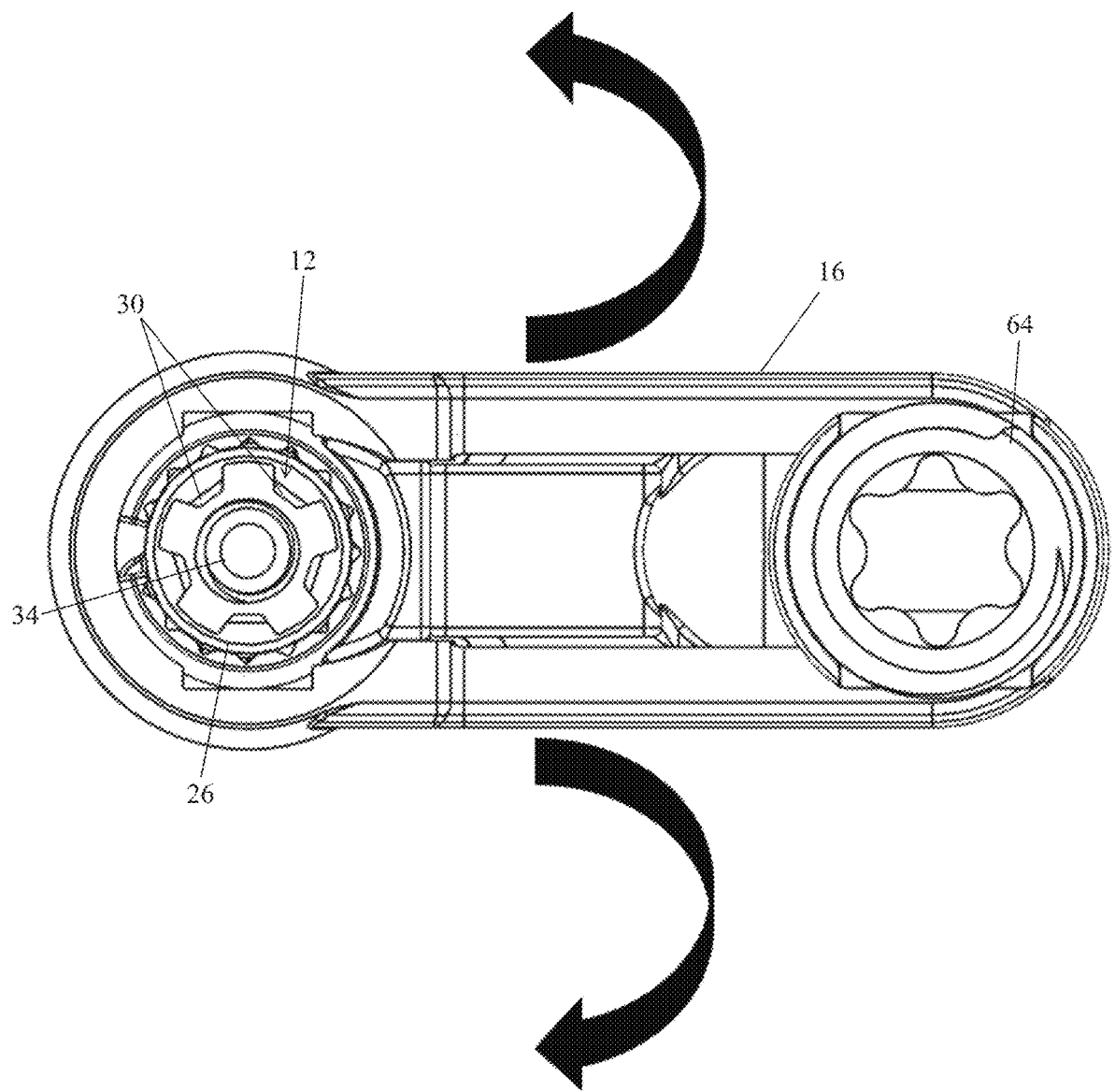

As represented in FIG. 17, the connector 16 can rotate clockwise or counter clockwise about the post 26 of the screw 12.

Figure 18:
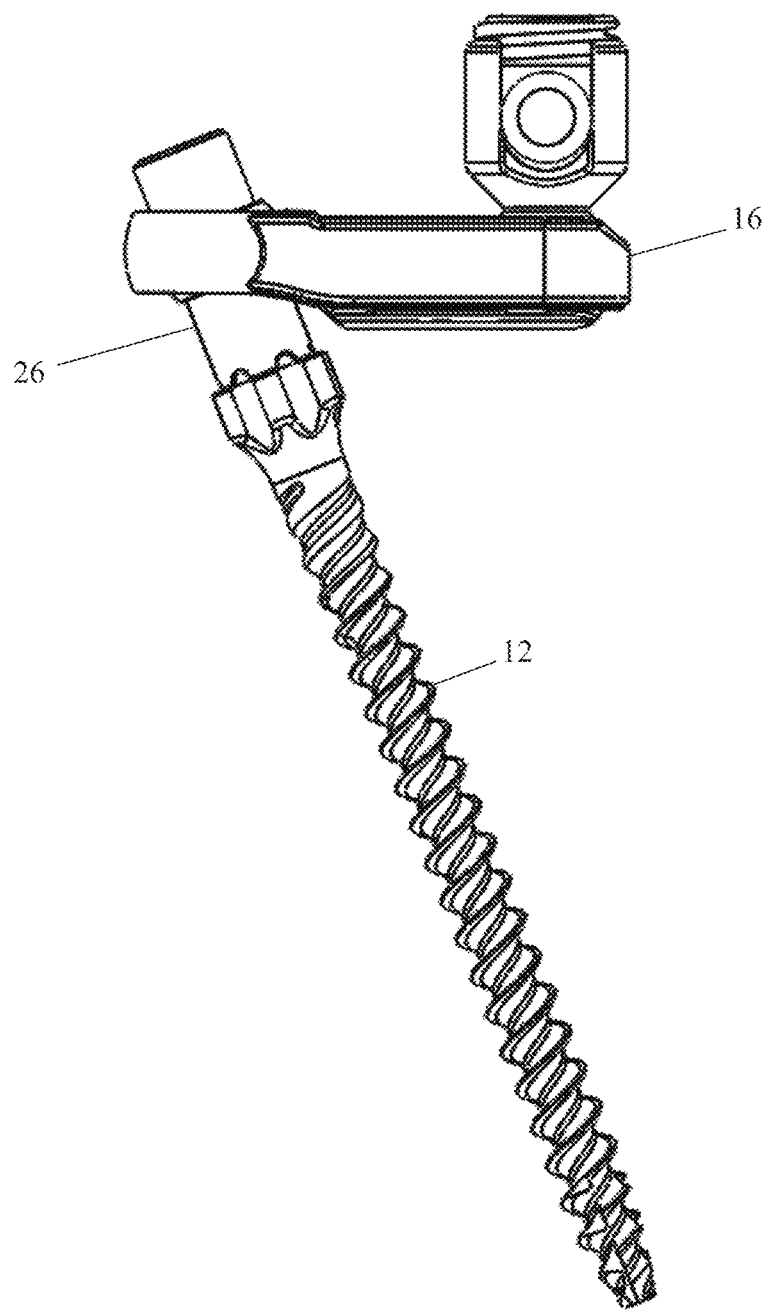

As represented in FIG. 18, the connector 16 can move polyaxially about the post 26 of the screw 12.

Figure 19:
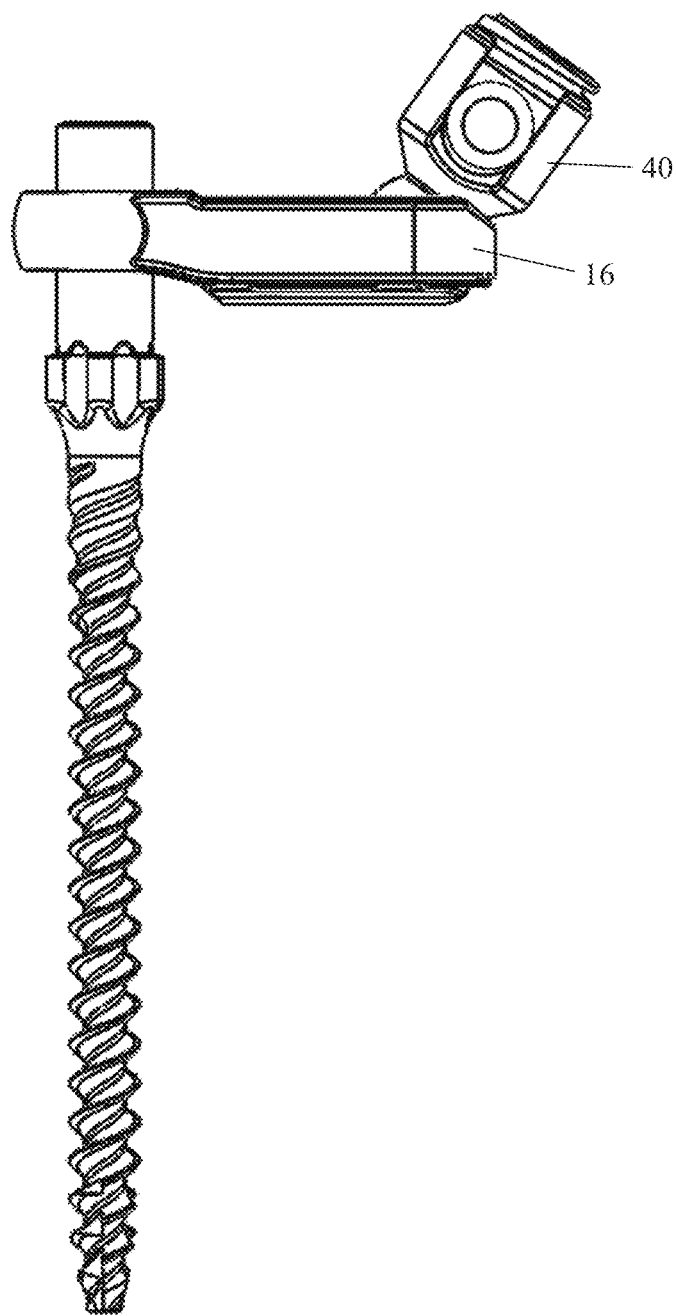

As represented in FIG. 19, the tulip housing 40 can angulate relative to the connector 16 in the medial and lateral directions.

Figure 20:
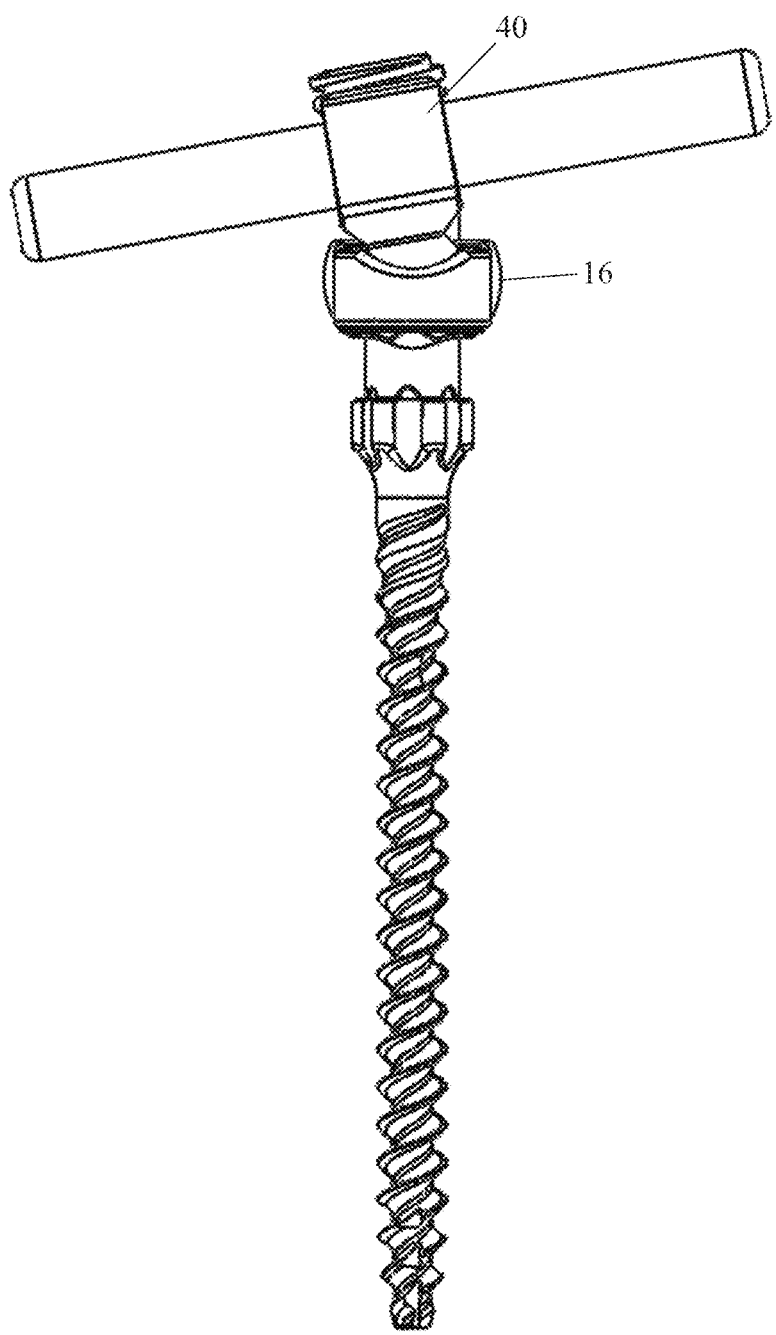

As represented in FIG. 20, the tulip housing 40 can angulate relative to the connector 16 in the cephalad and caudal directions.

Figure 21:
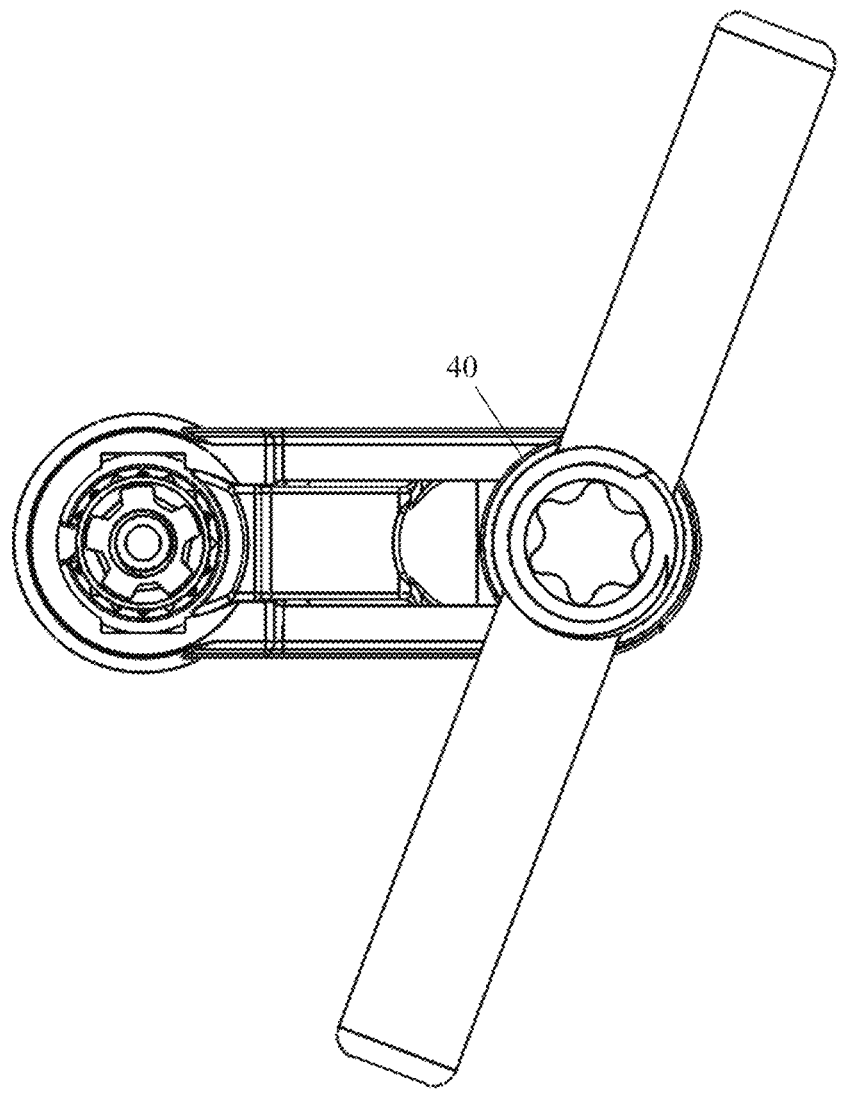

As represented in FIG. 21, the tulip housing 40 can rotate about its axis.

Figure 22:
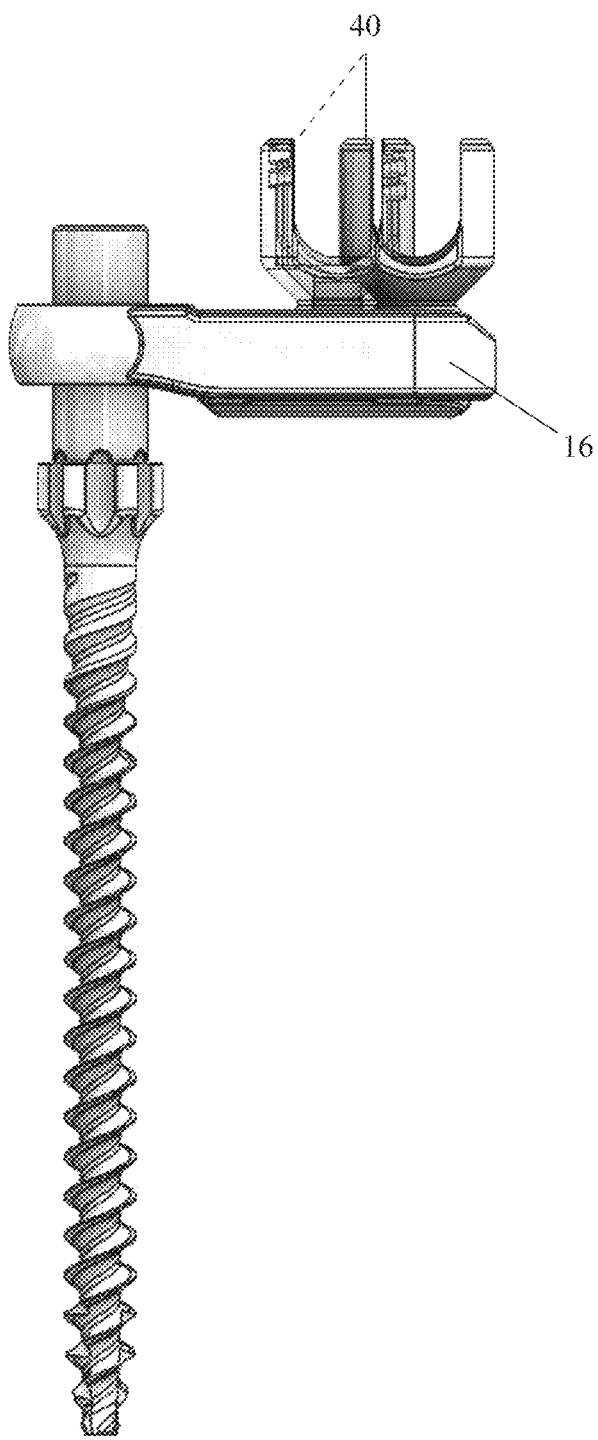
Figure 23:
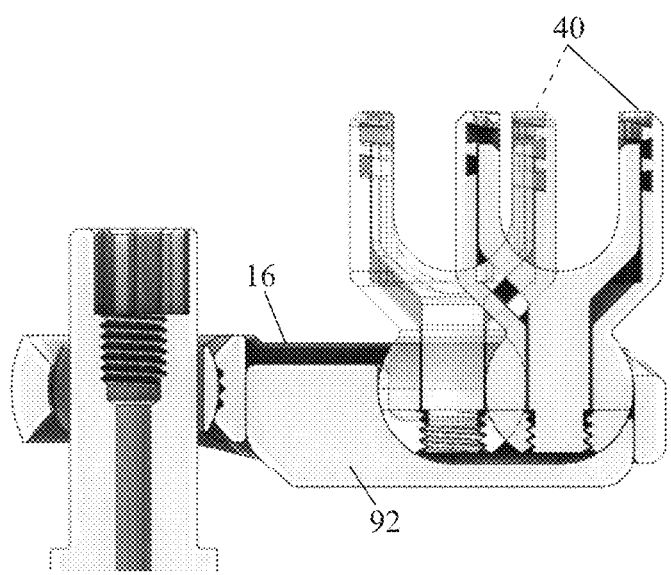

As represented in FIGS. 22 and 23, the tulip housing 40 can slide or translate within the connector 16.

Figure 25:
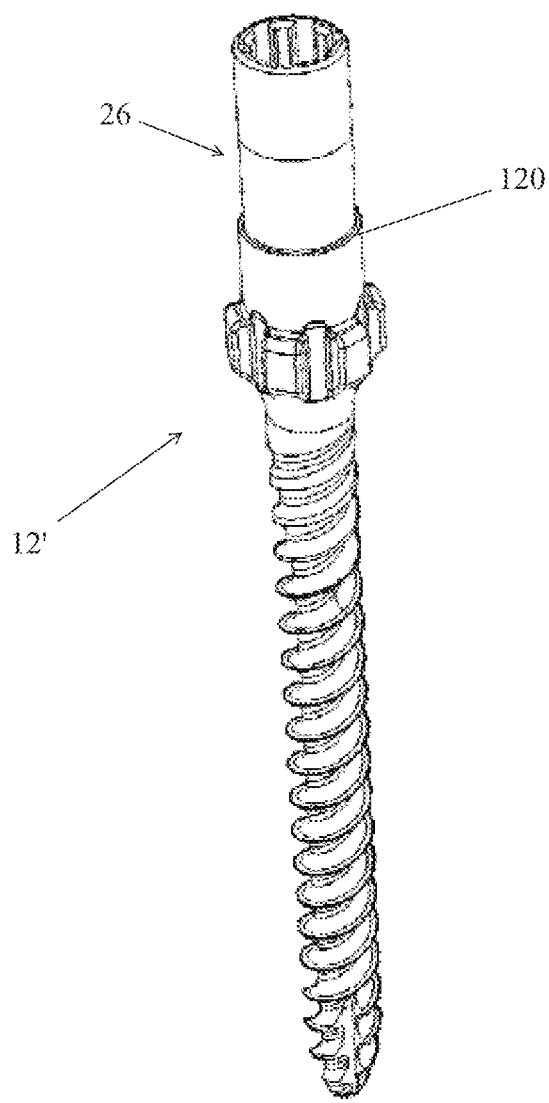
FIG. 25 is a perspective view of an alternative embodiment of a pedicle screw for use in implant systems according to the disclosure.
Figure 26:
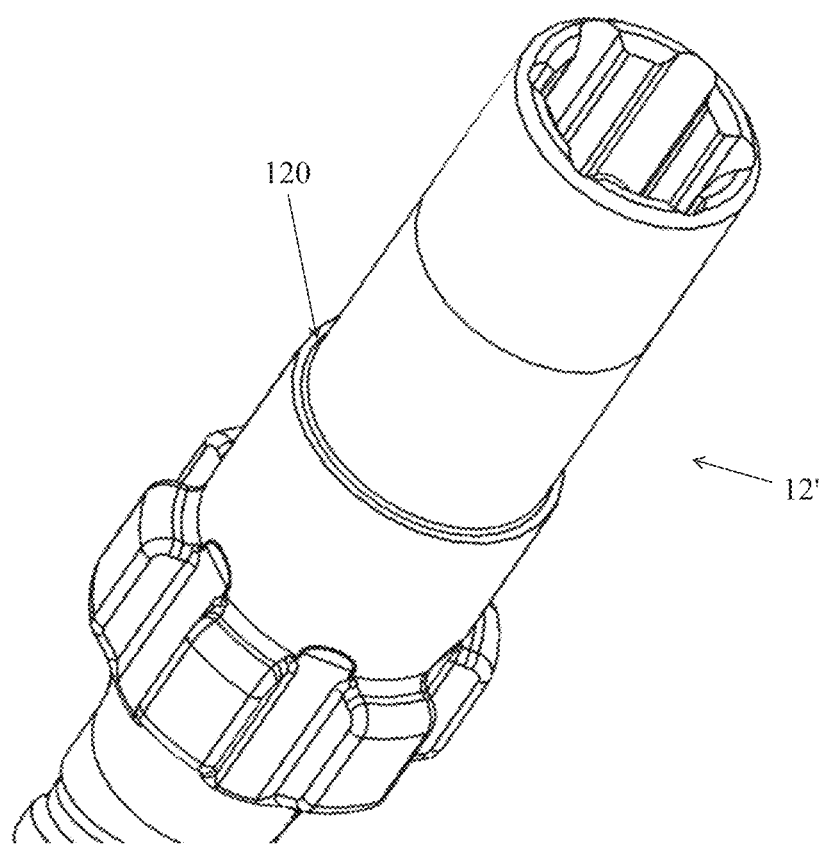
FIG. 26 is a close-up view of a portion of the pedicle screw of FIG. 25.
Figure 27:
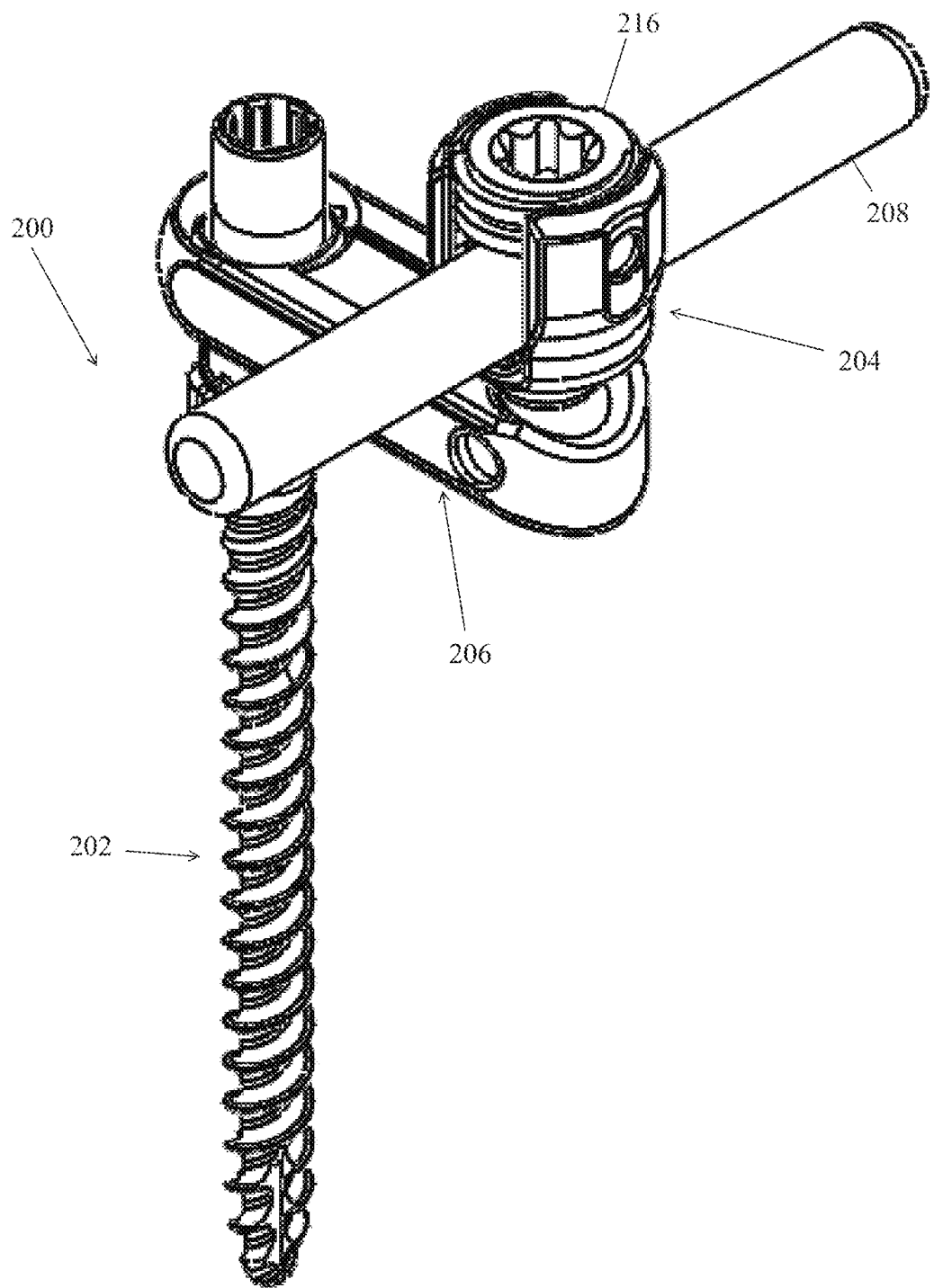
FIG. 27 shows an alternate embodiment of a posterior spinal implant system according to the disclosure.
Figure 28:
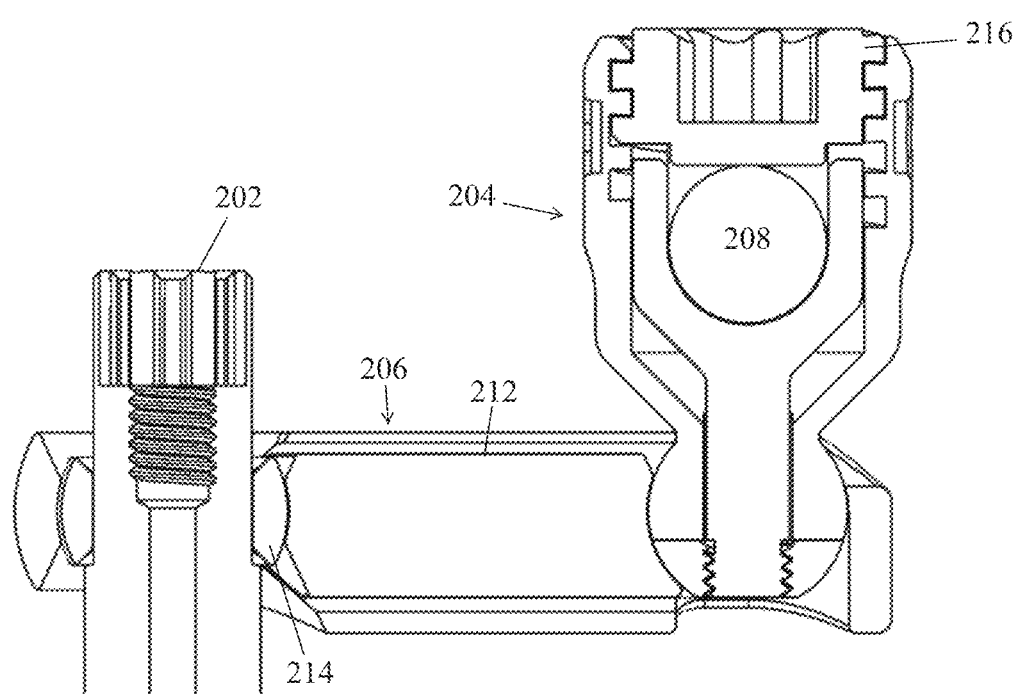
FIG. 28 is a cross-sectional view of the implant system of FIG. 27.
Figure 29:
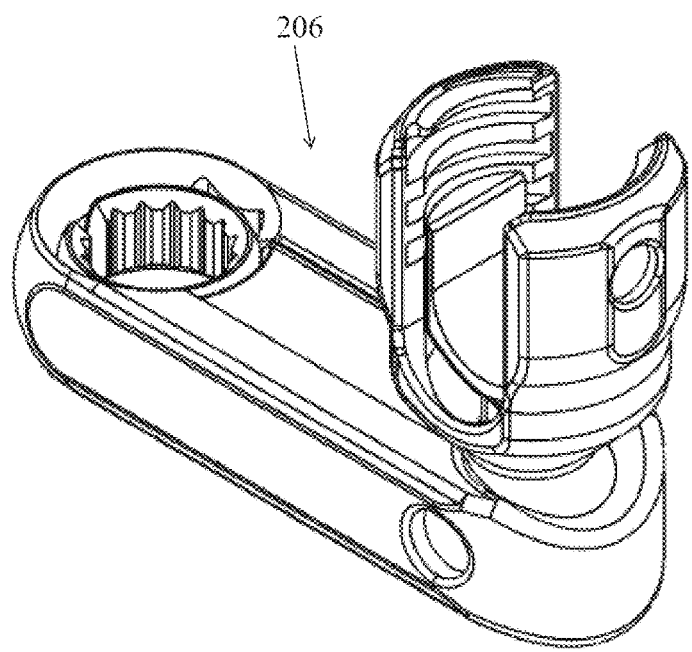
FIGS. 29-31 show components of the implant system of FIG. 27.
Figure 30:
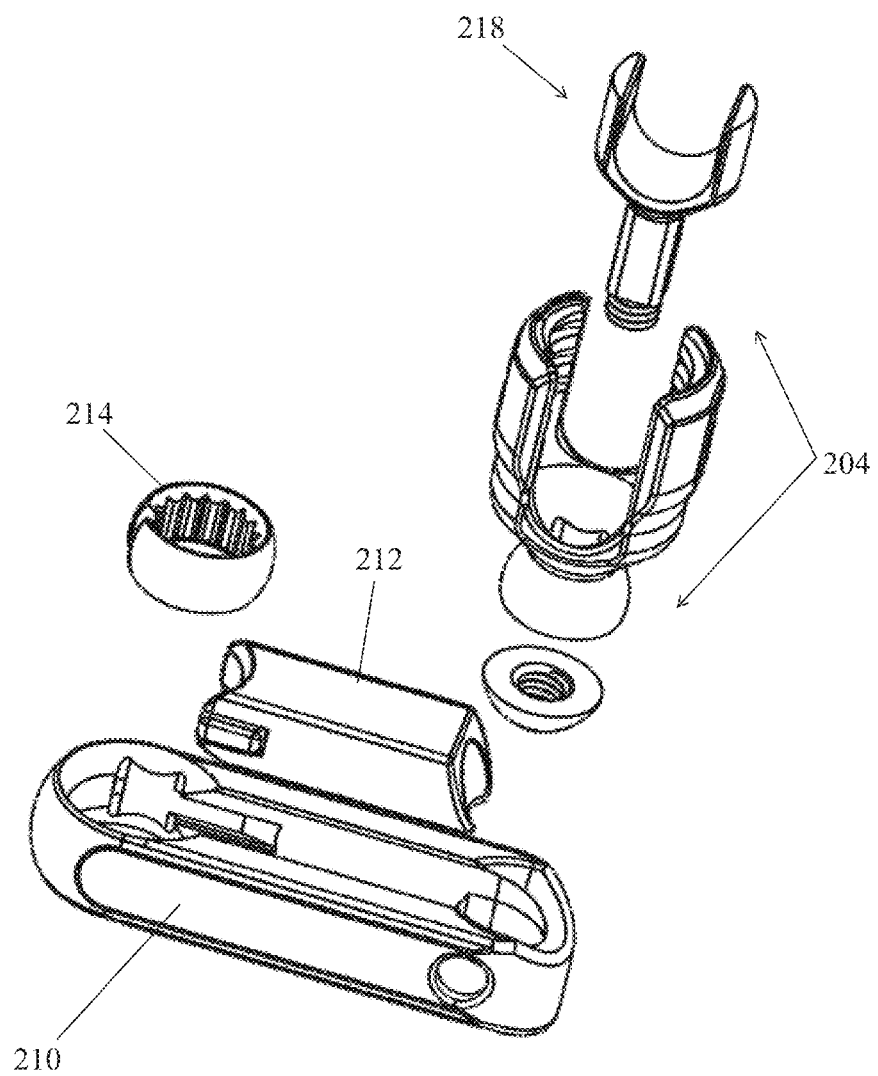
Figure 31:
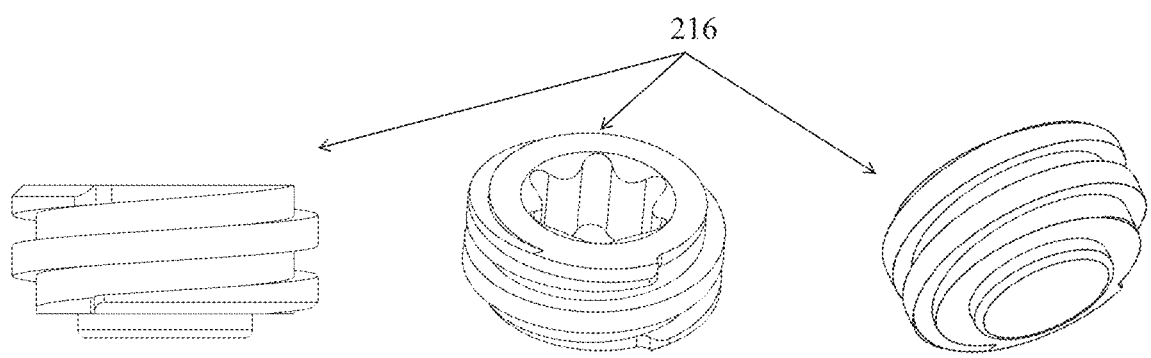

FIGS. 25 and 26 show an alternate embodiment of a pedicle screw 12' for use in implant systems according to the disclosure. The screw 12' is identical to the screw 12, except it includes a ledge 120 on the post 26. The ledge 120 provides a stop for the connector 16 during installation. This placement of the connector 16 abutting the ledge 120 maximizes the allowable angulation of the connector 16 relative to the post 26 of the screw 12'.

FIGS. 27-31 show an alternate embodiment of a posterior spinal implant system 200 according to the disclosure. The implant system 200 includes a pedicle screw 202, a polyaxial rod receiver 204, a connector 206, and a spinal rod 208. The pedicle screw 202 corresponds to the pedicle screw 12'. The receiver 204 corresponds to the polyaxial rod receiver 14. The spinal rod 208 corresponds to the spinal rod 18. The connector 206 includes an elongate body 210, and an elongated piston 212, and a polyaxial screw receiver 214 having a set screw 216. The receiver 214 also includes a yoke 218, corresponding to the yoke 42. The implant system 200 is installed and locked in a single step, as in the manner described in connection with the implant system 10.

The implant system 200 is similar to the implant system 10, except it does not include a component corresponding to the wedge 92 component of the system 10, and the component corresponding to the piston component of the system 10 has been lengthened to fill the space of the removed wedge 92. The wedge 92 as described in connection with the system 10 provided translational movement of the polyaxial rod receiving member 14. Thus, removal of the wedge 92 as described in connection with the system 200 results in a loss of the translational movement, such as shown in FIGS. 22 and 23 for the system 10. Thus, the system 200 is configured for applications not requiring the described translational movement. The other adjustments and movements as described previously for the system 10 and shown in FIGS. 16-21 will be understood to be applicable to the system 200.

Figure 32:
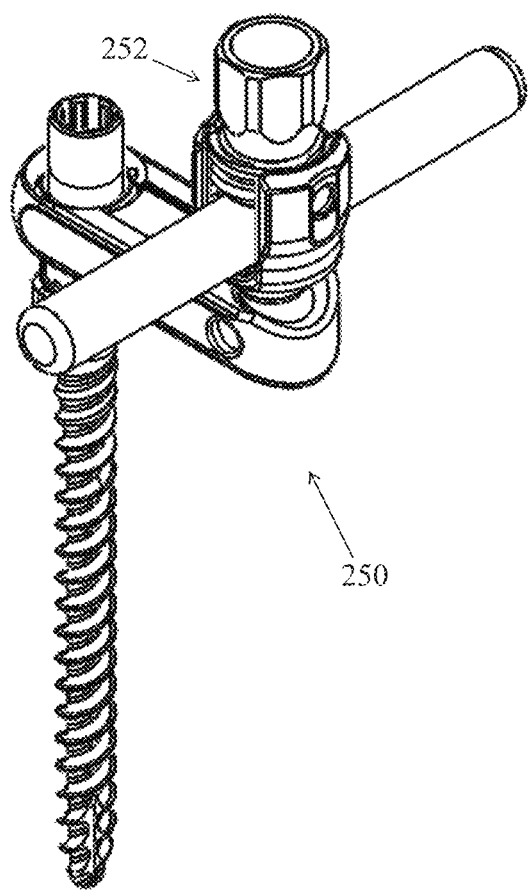
FIG. 32 shows an alternate embodiment of a posterior spinal implant system according to the disclosure.
Figure 33:
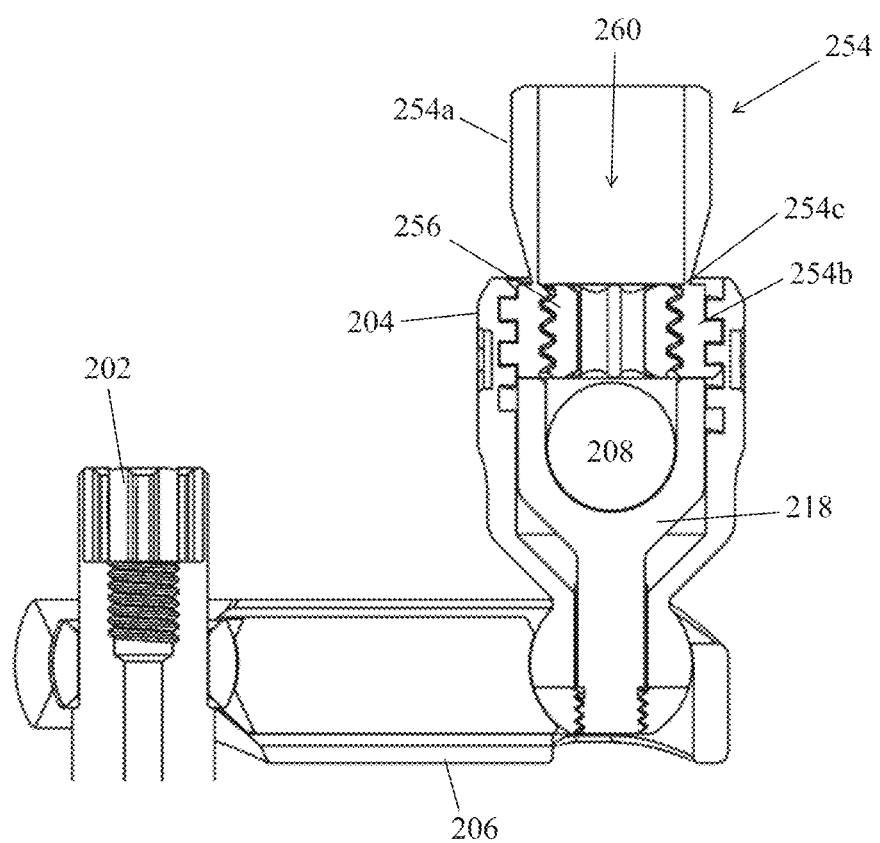
FIG. 33 is a cross-sectional view of the implant system of FIG. 32.
Figure 34:
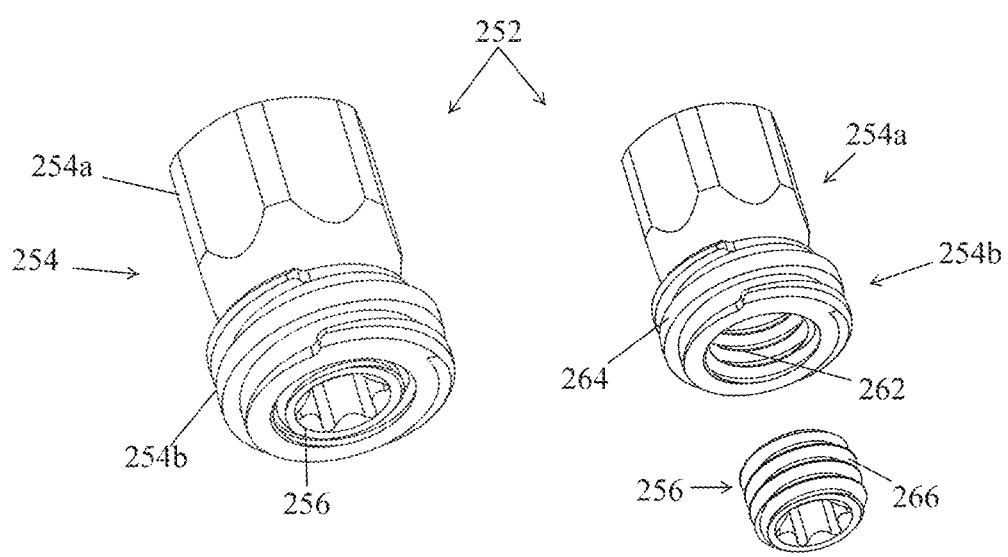
FIG. 34 shows a screw component of the implant system of FIG. 27.

FIG. 32-34 show another alternate embodiment of a posterior spinal implant system 250 according to the disclosure. The implant system 250 is identical to the implant system 200, except the set screw 216 is replaced with a two-stage set screw 252. Thus, it will be understood that the implant system 250 includes the pedicle screw 202, the polyaxial rod receiver 204, the connector 206, and the spinal rod 208.

The two-stage set screw 252 includes a first stage set screw 254 having an upper hex portion 254a and a lower set screw section 254b, and a second stage set screw 256. The first stage set screw 254 includes a central through-bore 260. The lower set screw section 254b has internal threads 262 and external threads 264. External threads 266 of the second stage set screw 260 are received by the internal threads 262 so that the two-stage set screw 252 is provided as a nested couple. As seen in FIG. 33, the upper hex portion 254a is connected to the lower set screw section 254b by a thin break point 254c to enable the upper hex portion 254a to break away from the lower set screw section 254b at a desired torque.

The two-stage set screw construction of the system 250 functions in the same manner as the single-stage set screw construct of the systems 10 and 200, with the exception that the locking function can be completed in two phases via the two-stage set screw 252. The first phase of the locking process locks the angulation/orientation of the tulip housing relative to the connector body, as well as the angulation/orientation of the connector body relative the screw post. The rod is free, such that the screw/connector sub-assembly can be rotated about the rod or translated along the rod for correction of the spine. This is accomplished by engaging the first stage set screw 254. The second stage set screw 256 is then engaged and locked onto the rod 208, once the user is satisfied with the desired spinal corrections.

In operation, the first stage set screw 254 rests against the yoke 218, while the second stage set screw 256 is nested inside it, not in contact with the rod 208. Actuation of the yoke only will result in the previously-described first phase of the locking process. The second stage set screw 256 is then engaged to lock the rod 208 in place, as previously described. When locking is complete, the user will use an instrument to apply sufficient torque to break off the hex portion 254a of the first stage set screw 254, such that the remaining portion is flush with the top of the tulip housing.

The adjustments and movements as described previously for the system 10 and shown in FIGS. 16-21 will be understood to be applicable to the system 250.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated.

The invention claimed is:

1. A posterior spinal implant system configured to immobilize and stabilize spinal segments, comprising:
   a pedicle screw;
   a spinal rod; and
   a connector connecting the pedicle screw to the spinal rod in a laterally spaced relationship with the spinal rod offset from a longitudinal axis of the pedicle screw, the connector comprising:
   an elongate connector body,
   a polyaxial screw receiver positioned in the connector body and configured to receive the pedicle screw and permit polyaxial orientation of the connector relative to the pedicle screw,
   a polyaxial rod receiver positioned in the connector body and configured to receive the spinal rod and permit polyaxial orientation of the spinal rod relative to the connector,
   a piston positioned in the connector body and located between the polyaxial screw receiver and the polyaxial rod receiver for engaging the polyaxial screw receiver, and
   a lock installed in the polyaxial rod receiver and operable to lock the connector relative the pedicle screw, lock the polyaxial rod receiver relative to the connector, and lock the spinal rod relative to the polyaxial rod receiver.

2. The spinal implant system of claim 1, wherein the lock comprises a set screw threadably installed on the polyaxial rod receiver and operable in a single step to simultaneously lock the connector relative the pedicle screw, lock the polyaxial rod receiver relative to the connector, and lock the spinal rod relative to the polyaxial receiver.

3. The spinal implant system of claim 1, wherein the lock comprises a set screw operable in two steps to lock the connector relative the pedicle screw, lock the polyaxial rod receiver relative to the connector, and lock the spinal rod relative to the polyaxial receiver.

4. The spinal implant system of claim 3, wherein the set screw comprises a two-stage set screw having a first stage set screw having an upper portion and a lower set screw section, and a second stage set screw nested within the lower set screw section, wherein the upper portion is configured to break away from the lower set screw section at a desired torque.

5. The spinal implant system of claim 1, wherein the polyaxial rod receiver comprises a tulip housing configured for receiving the spinal rod and having a spherical base, a yoke, and an end cap installable on the yoke and having a spherical sidewall, wherein the end cap is installed on the yoke, the spherical base of the tulip housing and the spherical sidewall of the end cap combine to provide a sphere for seating in the connector.

6. The spinal implant system of claim 1, wherein the connector further comprises a wedge member located adjacent the piston opposite the polyaxial screw receiver and configured to engage the polyaxial rod receiver to facilitate polyaxial range of motion or translational range of motion or both of the polyaxial rod receiver relative to the connector.

7. A posterior spinal implant system configured to immobilize and stabilize spinal segments, comprising:
   a pedicle screw;
   a spinal rod; and
   an elongate connector connecting the pedicle screw to the spinal rod in a laterally spaced apart relationship with the spinal rod offset from a longitudinal axis of the pedicle screw, the connector comprising:
   a connector body,
   a polyaxial screw receiver positioned in the connector body and configured to receive the pedicle screw and permit polyaxial orientation of the connector relative to the pedicle screw,
   a polyaxial rod receiver positioned in the connector body and configured to receive the spinal rod and permit polyaxial orientation of the spinal rod relative to the connector, and
   a set screw installed in the polyaxial rod receiver and operable in two steps to lock the connector relative the pedicle screw, lock the polyaxial rod receiver relative to the connector, and lock the spinal rod relative to the polyaxial receiver.

8. The spinal implant system of claim 7, wherein the set screw comprises a two-stage set screw having a first stage set screw having an upper portion and a lower set screw section, and a second stage set screw nested within the lower set screw section, wherein the upper portion is configured to break away from the lower set screw section at a desired torque.

9. The spinal implant system of claim 7, wherein the polyaxial rod receiver comprises a tulip housing configured for receiving the spinal rod and having a spherical base, a yoke, and an end cap installable on the yoke and having a spherical sidewall, wherein the end cap is installed on the yoke, the spherical base of the tulip housing and the spherical sidewall of the end cap combine to provide a sphere for seating in the connector.

10. The spinal implant system of claim 7, wherein the connector further includes a piston positioned in the connector body and located between the polyaxial screw receiver and the polyaxial rod receiver, the piston having a curved front surface for engaging the polyaxial screw receiver.

11. The spinal implant system of claim 10, wherein the connector further comprises a wedge member located adjacent the piston opposite the polyaxial screw receiver and configured to engage the polyaxial rod receiver to facilitate polyaxial range of motion or translational range of motion or both of the polyaxial rod receiver relative to the connector.

* * * * *